USOO5612188A

United States Patent [19]
Shuler et al.

[11] Patent Number: 5,612,188
[45] Date of Patent: Mar. 18, 1997

[54] AUTOMATED, MULTICOMPARTMENTAL CELL CULTURE SYSTEM

[75] Inventors: Michael L. Shuler, Ithaca; John G. Babish, Brooktondale, both of N.Y.; Lisa M. Sweeney, White Bear Lake, Minn.; Brian E. Johnson, Spencer, N.Y.

[73] Assignee: Cornell Research Foundation, Inc., Ithaca, N.Y.

[21] Appl. No.: 194,792

[22] Filed: Feb. 10, 1994

Related U.S. Application Data

[63] Continuation of Ser. No. 66,823, May 24, 1993, abandoned, which is a continuation-in-part of Ser. No. 799,044, Nov. 26, 1991, abandoned, which is a continuation-in-part of Ser. No. 797,311, Nov. 25, 1991, abandoned.

[51] Int. Cl.[6] .................. C12Q 1/00; C12M 1/34
[52] U.S. Cl. ................ 435/29; 435/33; 435/286.5; 435/294.1; 435/374
[58] Field of Search ............... 364/413.1, 413.01; 435/313–315, 284, 286, 287, 291, 299, 32, 29, 285, 240.2, 3, 284.1, 286.5, 286.6, 287.1, 289.1, 294.1, 297.2, 297.4, 303.1, 1.1, 1.2, 33; 436/63

[56] References Cited

U.S. PATENT DOCUMENTS

| | | |
|---|---|---|
| 3,300,386 | 1/1967 | Aron-Brunetiere et al. |
| 3,313,290 | 8/1963 | Chance et al. |
| 3,722,504 | 3/1973 | Sawyer. |
| 4,225,671 | 9/1980 | Puchinger et al. ............. 435/297.2 |
| 4,446,229 | 5/1984 | Indech ..................... 435/1 |
| 4,537,860 | 8/1985 | Tolbert et al. ............. 435/240.241 |
| 4,610,878 | 9/1986 | Wilson et al. |
| 4,629,686 | 12/1986 | Gruenberg ................. 435/284 |
| 4,650,766 | 3/1987 | Harm et al. ................ 435/284 |
| 4,673,650 | 6/1987 | William .................... 435/284 |

(List continued on next page.)

FOREIGN PATENT DOCUMENTS

| | | |
|---|---|---|
| 2431918 | 1/1976 | Germany. |
| 8203227 | 9/1982 | WIPO. |
| 9102049 | 2/1991 | WIPO. |

OTHER PUBLICATIONS

D'Souza et al: "Physiological Model for Tissue...";©1988; *Journal of Pharm. and Exper. Thera.*, vol. 245, No. 2; pp. 563–568.

J. Lehmann et al: "Bubble–free Reactors and their ..."; *Animal Cell Biotech.*, vol. 3; copyright 1988; pp. 221–237.

R.J. Riley, et al., "Bioactivation of Dapsone to a Cytotoxic Metabolite: in vitro use of a novel two compartment system which contains human tissues," *Br. J. clin Pharmac.* 30:417–26 (1990).

*Primary Examiner*—William H. Beisner
*Attorney, Agent, or Firm*—Nixon, Hargrave, Devans & Doyle

[57] ABSTRACT

The present invention relates to an in vitro system for physiological and metabolic evaluation of substances for use in living beings. The system includes one or more cell culture chambers, each containing cells in a culture medium and a gas-liquid exchange device for contacting the culture medium with oxygen-containing gas so that the culture medium absorbs that gas and desorbs carbon dioxide-containing gas. The conduit system conducts culture medium between the gas-liquid exchange device and the cell culture chambers. A circulation mechanism is used to circulate culture medium through the conduit system, the cell culture chambers, and the gas-liquid exchange device. In use, the substance to be evaluated is added to the culture medium of the system and circulated through the system. The cells in each of the cell culture chambers are then evaluated for effects resulting from the presence of the substance.

26 Claims, 23 Drawing Sheets

U.S. PATENT DOCUMENTS

| | | | |
|---|---|---|---|
| 4,720,462 | 1/1988 | Rosenson | 435/285 |
| 4,734,372 | 3/1988 | Rotman | 435/291 |
| 4,737,455 | 4/1988 | De Baetselier . | |
| 4,749,654 | 6/1988 | Karrer et al. | 435/240.21 |
| 4,835,102 | 5/1989 | Bell et al. | 435/29 |
| 4,929,542 | 5/1990 | Risley . | |
| 5,002,890 | 3/1991 | Morrison | 435/286 |
| 5,108,926 | 4/1992 | Klebe | 435/204 |
| 5,160,490 | 11/1992 | Naughton et al. | 435/284 |
| 5,316,905 | 5/1994 | Mori et al. | 435/3 |

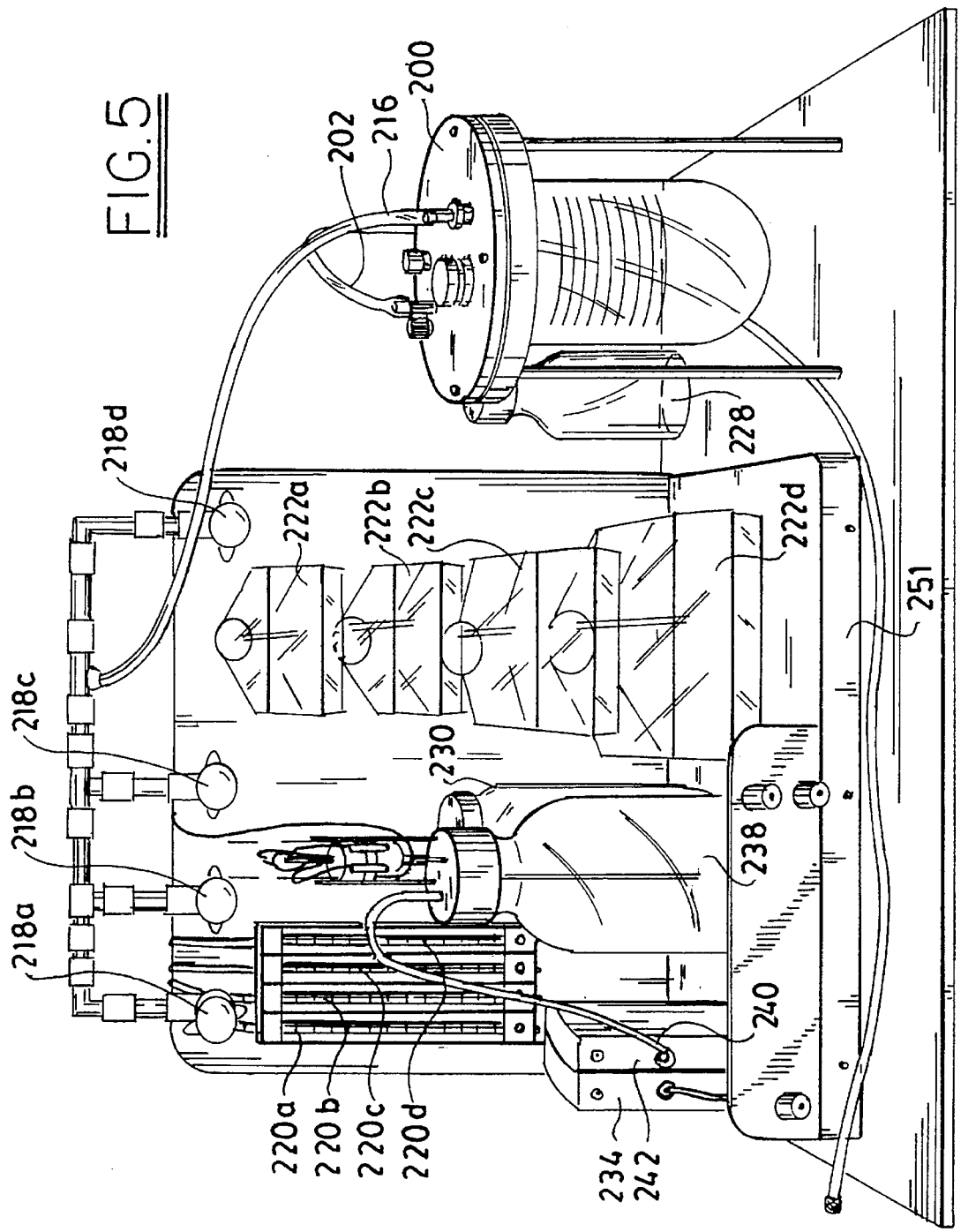

ns.
AUTOMATED, MULTICOMPARTMENTAL CELL CULTURE SYSTEM

The subject matter of this application was developed under a grant from the National Science Foundation (Award No. BCS9016798).

This application is a continuation of U.S. patent application Ser. No. 08/066,823, filed May 24, 1993 (now abandoned), which is a Continuation-In-Part of U.S. patent application Ser. No. 07/799,044, filed Nov. 26, 1991 (now abandoned), which is a Continuation-In-Part of U.S. patent application Ser. No. 07/797,311, filed on Nov. 25, 1991 (now abandoned).

FIELD OF THE INVENTION

The present invention is directed to an in vitro system for physiological and metabolic evaluation of substances for use in living beings.

BACKGROUND OF THE INVENTION

The use of living cells in culture for biomedical research was first introduced by Dr. Otto Warburg in the 1920's. Today, this technique enables scientists to model specific biochemical or physiological properties of cells under defined and reproducible conditions. Cell culture technology has made possible the study of many diseases independent of either patient or animal models. The obvious advantage of this methodology is that a variety of experiments can be performed while avoiding the moral dilemma of using human beings or animals as research tools.

Currently, both human and animal cell lines serve as surrogates for living organisms in screening the efficacy or toxicity of pharmaceuticals, agri-chemicals, and nearly all chemicals used in consumer products. The rapidly proliferating area of in vitro alternatives to animal testing utilizes cell culture techniques to model such toxic responses as skin and eye irritation.

While cell culture technology has given science the ability to perform research not possible at the beginning of this century, it has significant inherent limitations. As a result, cell culture methods have not superseded research on humans or animals as the ultimate predictor of biological response. One limitation is that current techniques of exposing and dosing cell cultures yield results which lack a physiologically based foundation. As a result, such exposure methods are not equivalent to the physiologic pattern of exposure encountered by cells in a living being. More particularly, present cell culture techniques are not able to duplicate the metabolism of dose regimens in living organisms where concentrations are greatest immediately following exposure and decline until the cell culture is subsequently exposed to that substance. As a result, it is not possible to determine whether pharmacological changes or damage induced at peak concentrations will be reversed as concentration falls and the cell returns to a pre-exposure status.

Within living beings, concentration and time interact to influence the intensity and duration of a desired pharmacologic response or toxic manifestation. With respect to exposure to toxic substances, many types of cells undergo a biotransformation reaction to protect them from chemical damage. For example, cells, which utilize glutathione ("GSH") to protect themselves against chemical damage, may deplete GSH reserves when exposed to high concentrations of toxic chemicals. As a result, if subsequent exposures occur before repletion of GSH stores, the cell will manifest a toxic response. However, if there is sufficient time for replenishment of GSH reserves, no toxicity will develop. Thus, exposure frequency is as critical a determinant of cellular toxicity as the amount of exposure to a chemical. This characteristic waxing and waning of chemical exposure and resultant cellular responses cannot be mathematically stimulated based on the results of a cell culture experiment performed with static exposure concentrations.

SUMMARY OF THE INVENTION

The present invention relates to an in vitro system for physiological and metabolic evaluation of substances for use in living beings. The system includes one or more cell culture chambers each containing cells in a culture medium. A gas-liquid exchange device is also present in the system to cause the culture medium to contact and absorb oxygen-containing gas and to desorb carbon dioxide-containing gas. A conduit system conducts culture medium between the gas-liquid exchange device and the one or more cell culture chambers. A circulation mechanism causes the culture medium to circulate through the conduit system, the one or more cell culture chambers, and the gas-liquid exchange device. The cell culture chambers can contain a variety of different cell types, including lung cells and liver cells. Operation of the system is desirably controlled by a microprocessor.

In use, a substance to be evaluated is added to the culture medium. The culture medium containing the substance is then circulated through the cell culture chambers, the gas-liquid exchange device, and the conduit system with assistance by the circulation mechanism. After such circulation is completed, the cells in the culture chambers are evaluated for physiological changes resulting from the presence of the substance in the culture medium.

Uses of the multicompartmental cell culture system of the present invention are numerous. For example, it can determine the efficacy and toxicity simultaneously of a potential pharmaceutical drug, so that the therapeutic index of the drug will be immediately known. Accordingly, a drug that may initially appear to be promising, but whose development would eventually be terminated due to toxicity discovered following administration to humans or animals, can be eliminated immediately using the system of the present invention.

The multicompartmental cell culture system of the present invention is also useful in testing pro-drugs for both efficacy and their ability to be metabolically transformed into active moieties. For example, the system can contain hepatocytes with human biotransforming enzymes, as well as target cell types. In this manner, the multicompartmental cell culture system of the present invention will mimic the actual metabolism of a drug in a human or animal system.

In another example, the DNA component uridine (i.e., bromodeoxyuridine) can be administered and its differential uptake by normal and transformed cells assessed. By modeling several doses of test chemical, the optimal ratio of incorporation by neoplastic cells (H4IIE) with respect to normal cells (lymphocytes) can be determined.

With a knowledge of the volume of distribution (Vd) in the target organism (a human being for example), the optimal dose may be determined directly from the present invention by means of the relationship:

$$Dose = C_0 * Vd$$

where $C_0$ is the concentration at time zero in the system and dose is in mg/kg. In this way, the invention described allows the determination of dose directly in mg/kg as well as an estimate of the difference between effects on H4IIE cells (i.e., target cells) and normal lymphocytes (i.e., nontarget cells).

This model using uridine analogs can be adapted for the in vitro screening of anti-neoplastic drugs for efficacy against cancer cells. The present invention permits tumor cells and normal cells to be exposed to candidate anti-cancer drugs simultaneously, which will permit determination of a drug's ability to discriminate between the two cell types, prior to human or animal testing. Drugs which do not discriminate between cancer cells and normal cells can be eliminated immediately.

The system is also designed to permit determination of multiple dose regimens, because drugs are administered on the same mg/kg basis used for human drug dosages and clearance rates are physiologically based. Such multiple dose experiments would allow for the determination of additive as well as synergistic effects, such as enzyme induction or inhibition.

The multicompartmental cell culture system of the invention, besides useful for screening and studying the metabolic profile of a drug, can also be used to identify interactions with other drugs, foods, and food additives that effectively halt development of drugs in the final stages of clinical testing.

Another use for the multicompartmental cell culture system of the present invention is the determination of the effects of cellular metabolites of test chemicals on secondary cells. Such information is useful in the agrichemical and chemical industry. In this embodiment, the multicompartmental cell culture system of the present invention would have at least two cultures in separate chambers, namely hepatocytes (for example, human, rat or mouse) and pulmonary Clara cells (for example, human, rat or mouse). Reactive metabolites produced by the hepatocytes in the first culture may circulate and affect the pulmonary cells in the second culture, providing an in vitro, interactive model which mimics the intact mammalian system.

By modeling the chemical absorption, distribution, metabolism and elimination of animals or humans, a physiologically-based pharmacokinetic model (PBBK) system can be developed. The system of the present invention allows for drug, toxicant and metabolite communication among various cell and tissue types. The distribution and elimination of chemicals and their metabolites among the cells and tissues can be based upon human or animal physiological relationships. This system allows a close resemblance between the dose regimens of pharmaceuticals and exposure to environmental chemicals, as would be experienced in living systems. In living systems, these dose regimens and exposures would result in concentrations being greatest immediately following exposure and declining until the next exposure to the chemical. Metabolic processes within cells respond to the changes in concentration of the test chemical. Pharmacological changes or damage induced by a chemical at peak concentrations may be reversed as the chemical concentration falls and the cell may return to pre-exposure status before the subsequent exposure to the chemical. The frequency of exposure is as critical a determinant of cellular toxicity as the amount of the exposure to a chemical. This characteristic waxing and waning pattern of chemical exposure and resultant cellular responses cannot be simulated by the application of mathematical functions to results of a cell culture experiment performed with static exposure concentrations, but this pattern can be produced in the multicompartmental cell culture system of the present invention. The monitoring and adjustments made to the model system of the invention permit a close resemblance to animal or human models without resorting to the use of living organisms.

BRIEF DESCRIPTION OF THE DRAWINGS

FIG. 5 is a detailed perspective view of the system of FIG. 4.

DETAILED DESCRIPTION OF THE INVENTION AND DRAWINGS

The present invention is directed to an in vitro system for physiological and metabolic evaluation of substances for use in living beings as well as the use of such a system in carrying out such evaluations.

Figure 1:
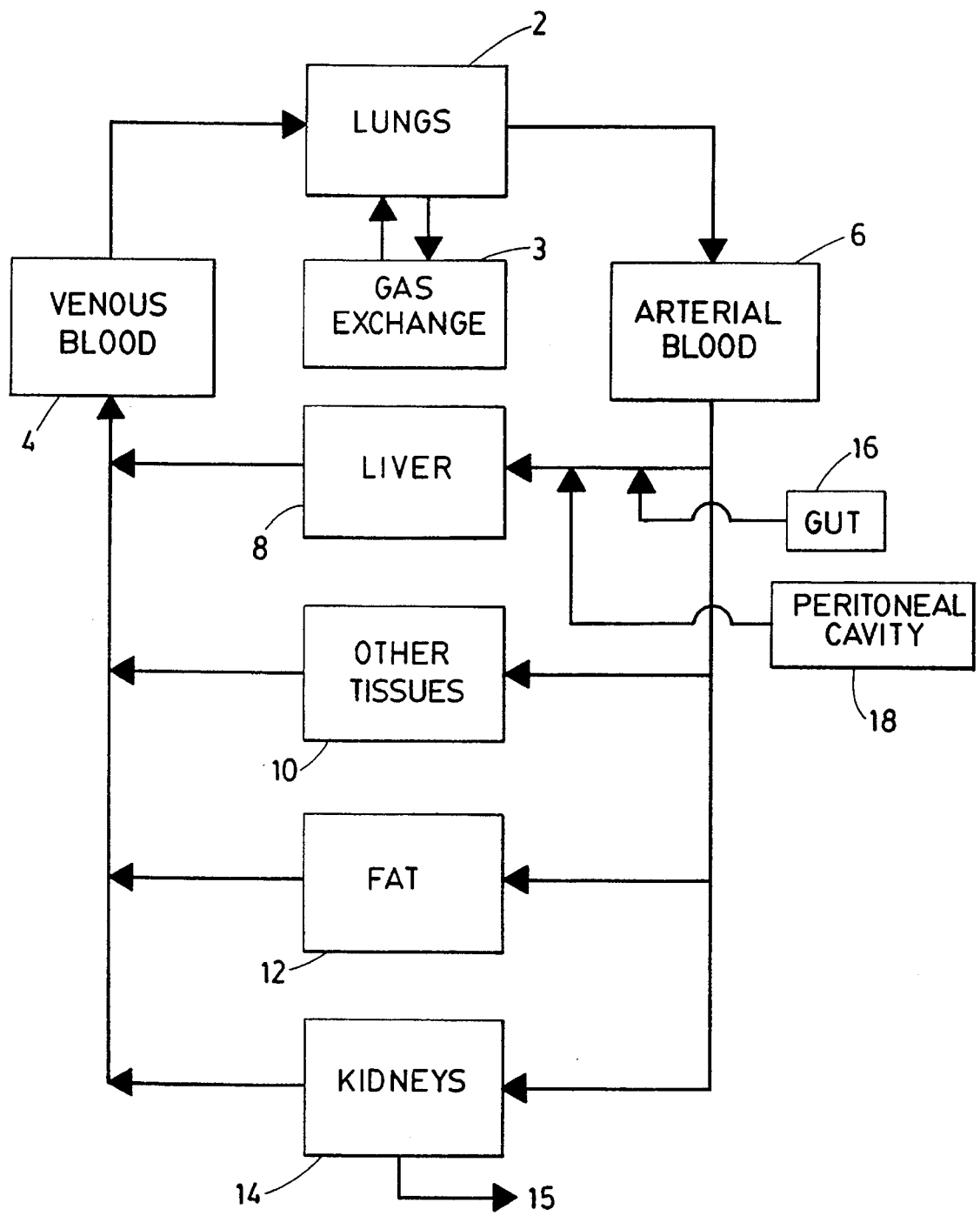
FIG. 1 is a block diagram of a system in accordance with the present/invention.

FIG. 1 is a block diagram of an in vitro system in accordance with the present invention. Lung cell simulating chamber 2 receives oxygenated culture medium from gas exchange device 3. Such oxygenated medium is obtained by contacting culture medium with oxygen-containing gas so that the culture medium absorbs oxygen-containing gas and desorbs carbon dioxide-containing gas. The culture medium exiting lung cell simulating chamber 2 is analogous to arterial blood 6 in mammals. The oxygen-containing culture medium constituting arterial blood 6 is then supplied to liver simulating chamber 8, other tissue simulating chamber 10, fat simulating chamber 12, and kidney simulating chamber 14. The culture medium departing from liver simulating chamber 8, other tissue simulating chamber 10, fat simulating chamber 12, and kidney simulating chamber 14 is analogous to venous blood 4 in mammals. As shown in FIG. 1, the culture medium corresponding to venous blood 4 is returned to lung cell simulating chamber 2. The system of the present invention also includes gut simulating chamber 16 and peritoneal cavity simulating chamber 18, both of which constitute sites for introduction of test compounds. As in mammals, waste liquid 15 is withdrawn from kidney simulating chamber 14.

Figure 2:
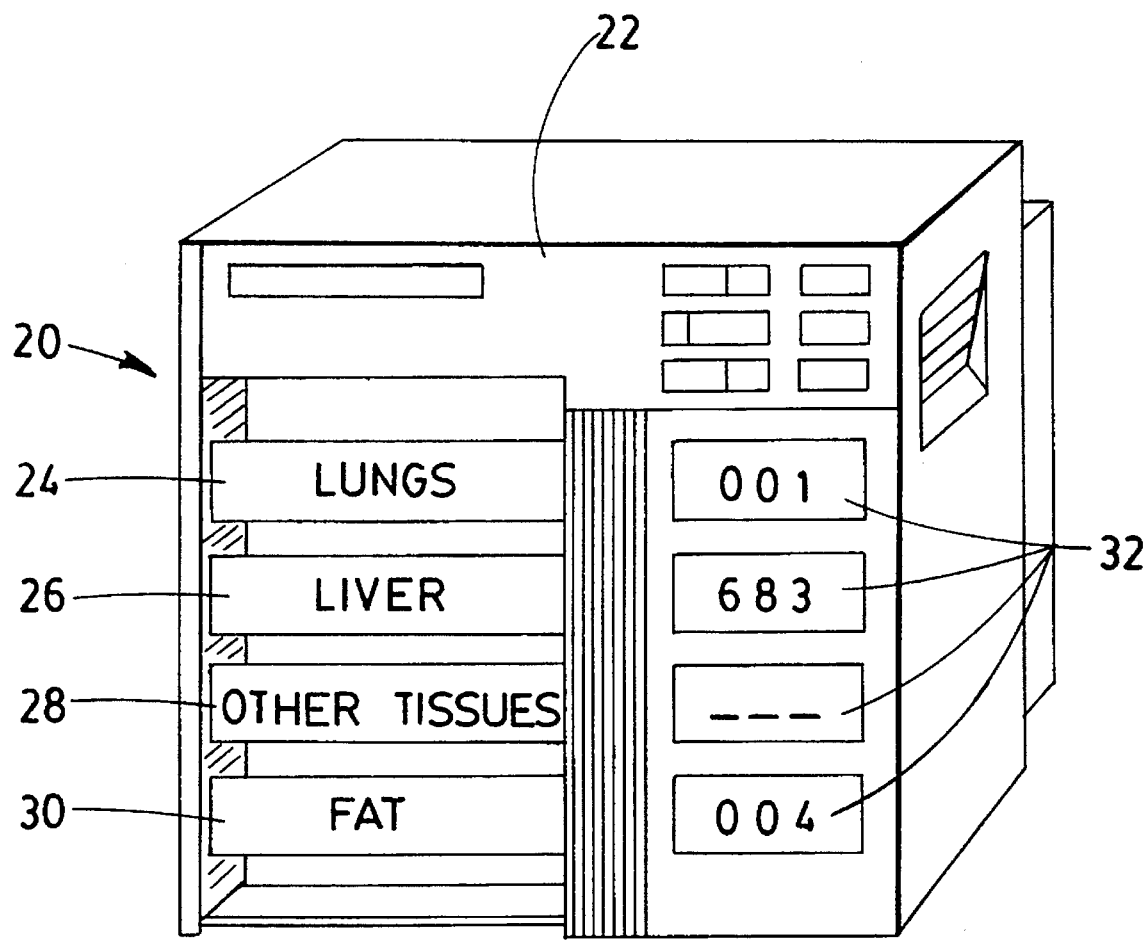
FIG. 2 is a simplified perspective view of one embodiment of the exterior of the system of the present invention.

FIG. 2 is a simplified perspective view of one embodiment of the system of the present invention. As shown, the system includes multicompartment cell culture system 20 having cabinet 22 with a first cell culture chamber 24 simulating lungs, a second cell culture chamber 26 simulating liver, a third cell culture chamber 28 simulating other tissues, and a fourth cell culture chamber 30 simulating fat. Cabinet 22 has a plurality of digital read-out indicators/controllers 32 to provide system operators with operational information.

Cells from any type of organism, which can be adapted to tissue culture, can be used in the system. These organisms include human beings, laboratory animals such as rats, mice, and hamsters, domestic farm laboratory animals, fish, insects, plants, unicellular organisms, and viruses. The choice of organisms is not meant to be limited by the preceding list. Particular embodiments can mix complete organisms in one or more compartments with cell, tissue, or organ cultures in one or more of the other compartments.

Cells from an organism with a particular condition can also be selected for inclusion within the system. Age, ethnicity, and gender are other aspects that can be considered in cell selection.

The system can also include cells that have been engineered in various ways. For example, the cells used could be a chimeric species (for example, human×mouse combinations) or can be cells transfected with foreign or altered genes.

To model the metabolic capacity of humans for any particular drug or chemical, a bank of four to five of the multicompartmental cell culture system units can be set up, each system representing a particular percentile of the population. Due to the genetic variation of humans with respect to xenobiotic metabolism, each of the units is set up to model the metabolism of a particular population segment. Segments can include the elderly, neonates, and pediatric population, as well as account for differences due to gender, ethnicity, or physical condition.

Figure 3:
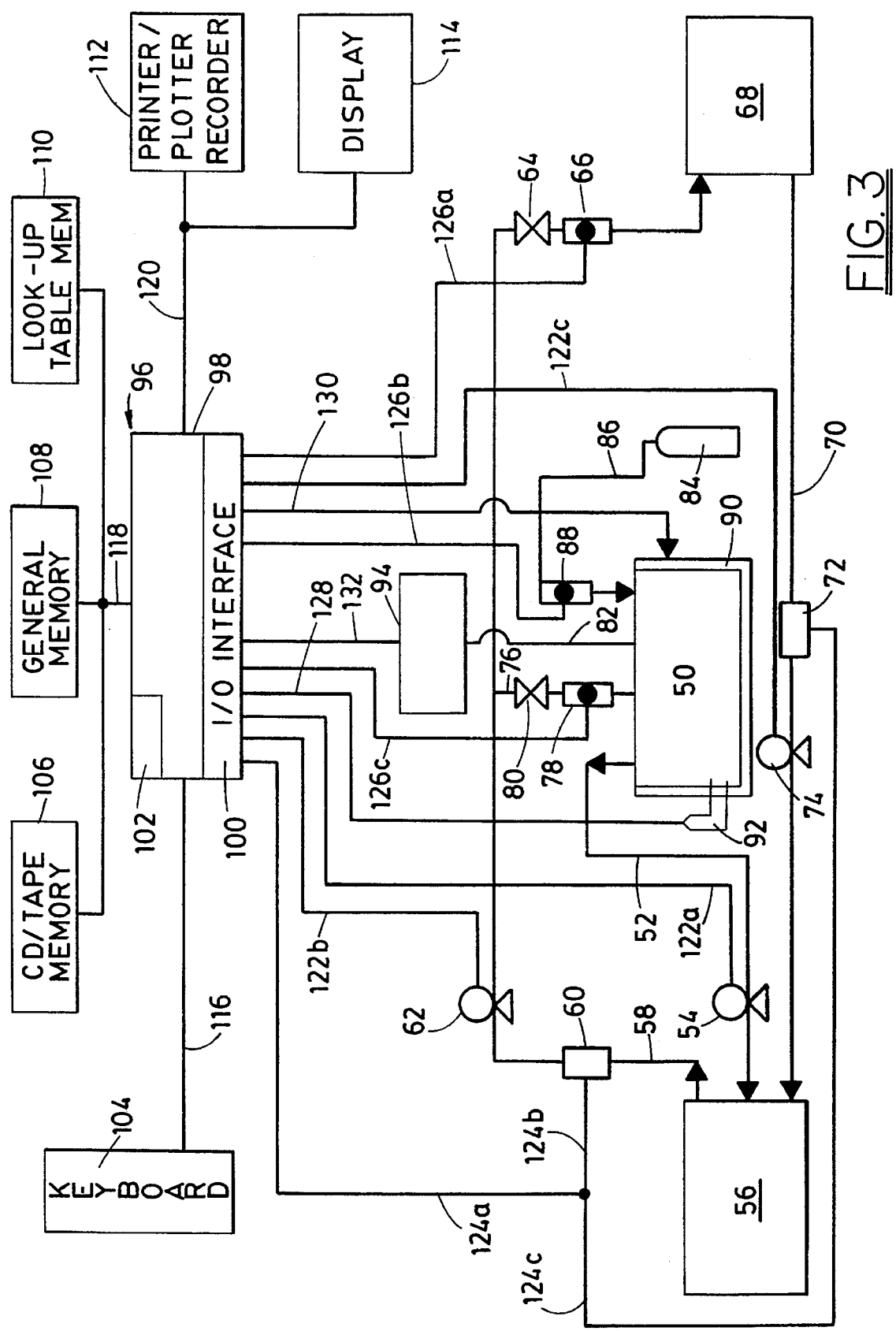
FIG. 3 is a detailed schematic view of one embodiment of the system of the present invention.

FIG. 3 is a detailed schematic view of one embodiment of the system of the present invention. In use, a test chemical is added to reservoir 50, containing any standard tissue culture medium having any type of serum (e.g., horse serum) and various surfactants. Liquid is withdrawn from reservoir 50 through reservoir discharge conduit 52 by pump 54 and fed to cell culture chamber 56. In one embodiment of the present invention, cell culture chamber 56 contains lung cells. Culture medium containing test chemical is withdrawn from cell culture chamber 56 through discharge conduit 58 and sensor 60 by pump 62. From pump 62, liquid passes through needle valve 64 and flow meter 66 before entering cell culture chamber 68. In one embodiment, cell culture chamber 68 contains kidney cells. Culture medium is withdrawn from cell culture chamber 68 through conduit 70 and sensor 72 by pump 74. Pump 74 returns culture medium containing test material to cell culture chamber 56. Instead of cycling culture medium containing test material to cell culture chamber 68, pump 62 can recycle this mixture to reservoir 50 through conduit 76, flow meter 78, and valve 80.

Liquid within reservoir 50 is oxygenated by causing oxygen-containing gas from supply tank 84 to flow through conduit 86 and flow meter 88 into reservoir 50. Gas, including carbon dioxide-containing gas desorbed from the culture medium, is exhausted from reservoir 50 through exhaust gas line 82.

Culture medium within reservoir 50 is maintained at an appropriate temperature by heater coil 122 within the wall of reservoir 50. Heater coil 122 operates in response to temperature probe 92.

As noted supra, the cell culture chambers of the present invention may contain a wide variety of cell types. In FIG. 3, cell culture chamber 56 may contain one of a variety of lung cells, including mouse pulmonary LL/2 cells obtained from the American Type Culture Collection (Rockville, Md.). Pulmonary Clara cells, pulmonary macrophages, or Type II cells are also suitable lung cells. Cell culture chamber 68 may also contain a variety of liver cells, such as H4IIE cells.

Biological, toxicological, and other effects induced by the test chemical on the cell cultures in chambers 56 and 68 can be monitored or discerned by means of in-line sensors 60 and 72. These devices monitor the culture medium in conduits 58 and 70, respectively. Sensors 60 and 72 can be any conventional liquid sensing device. Examples of such devices are spectrophotometers, pH meters, fluorometers, turbidity meters, etc.

A key feature of the in vitro system of the present invention as embodied by FIG. 3, is the presence of central computer 96 which monitors and regulates system operations. Central computer 96 includes microprocessor 98 provided with input/output interface 100 and internal register/cache memory 102. As shown, microprocessor 98 interfaces to keyboard 104 through connection 116, to non-volatile storage memory 106, general purpose memory 108, and look-up tables 110 through connector 118, and to printer/plotter recorder 112 and display 114 through connector 120.

Non-volatile storage memory 106 may be in the form of a CD writable memory, a magnetic tape memory, or the like.

Look-up tables 110 may physically comprise a portion of general purpose memory 108 which is set aside for storage of a set of mass balance equations applicable to various substances to be modeled in the system. These equations represent physiologically-based pharmacokinetic models for various biological/chemical substances in systems.

Internal register/cache memory 102 and general purpose memory 108 contain a system program in the form of a plurality of program instructions and special data for automatically controlling virtually every function in the system of the present invention.

Fluid flow monitoring lines 126a, 126b, and 126c provide inputs to microprocessor 98 through input/output interface 100 from flow meters 66, 88, and 78, respectively. This permits precise control over fluid flow rates within the system by adjustment of program commands which are transmitted to pumps 54, 62, and 74, through pump control lines 122a, 122b, and 122c, respectively. For example, the flow rates may be set to 9.5 mL/min. in conduit 58, 2.5 mL/min. through flow meter 66, 7 mL/min. through flow meter 78, and 2.5 mL/min. in conduit 70.

The temperature of culture medium in reservoir 50 is regulated by microprocessor 98 which receives, through input/output interface 100 and temperature indicator line 128, temperature measurements from temperature probe 92. In response to these signals, heater coil 90 is turned on and off by microprocessor 98 through input/Output interface 100 and heater coil control line 130.

Biological and toxicological reactions/changes in cell culture chambers 56 and 68 are detected by sensors 60 and 72, respectively, and communicated to microprocessor 98 through control lines 124a, 124b, and 124c as well as input/output interface 100. The sensors can be designed to represent test results in terms of specific values or ranges of wavelengths to represent test results.

Exhaust gas line 82 is provided with chemical/biological sensor 94 to generate an electrical signal for analysis of/control over chemical/biological activity in the system. This signal is carried by sensor indicator line 132 to input/output interface 100 and microprocessor 98.

An example of software suitable for operation of the in vitro system of FIG. 3 is described infra with reference to FIGS. 10–15.

Standardized cell culture chambers 56 and 68 will permit cell culture compartments, prepared with pre-identified species, cell type, etc., to be sent to test laboratories. Thus, researchers will need to do no more than simply order ready made, disposable compartments which they may simply plug into the system of FIG. 3., greatly facilitating and expediting research.

The software of the computer system of FIG. 3 is designed to model different physiological flow rates, and to reflect different pathological conditions, including a person at rest, during exercise, or at sleep.

The versatility of microprocessor 98 further extends to the display function which might provide display 114 with continuously updated readings from sensors 60 and 72 in the form of a number between 1 and 2 or as an anti-log number ranging between 0 to 100 or as alphanumeric text providing quantitative and qualitative information.

Microprocessor 98 is also quite easily adaptable to include a program to provide the researcher with interactive control via keyboard 104. This permits, for example, directing the computer to specifically check on the conditions of any of the culture compartments at any given time.

The system of the present invention may also be deployed for the purposes of taking measurements for determining whether healthy cells are in the midst of being transformed to cancerous cells and data relevant thereto. The diversity and flexibility of the present invention also permits carrying out tests using multiple cell culture chambers of parallel cell types to test the effects of an agent on different cell types simultaneously. The chambers may be filled with cell lines of different species, e.g., mouse, rat, human, or different organs, e.g., lung, heart, and kidneys, or of different populations, e.g., neonates, middle-aged, and elderly. Many other combinations of parallel cell cultures are feasible and useful.

A further option provided by the present invention is the ability to recall previously stored test results for similar experiments by recalling information from the CD/tape memory 106. Thus, memory 106 may be preprogrammed to hold historical data taken from published information, data gathered from previously run tests conducted with the system of the present invention or data derived from theoretical calculations.

The provision of the CD/tape memory also permits the system to be used as an information researching tool. It can, for example, obtain the research data pertaining to a particular test chemical, or to a particular culture line, etc., based on selection information inputted into microprocessor 98 via keyboard 104. By including or developing a large library of information in memory 106, researchers will be able to configure and plan test runs more intelligently.

Figure 4:
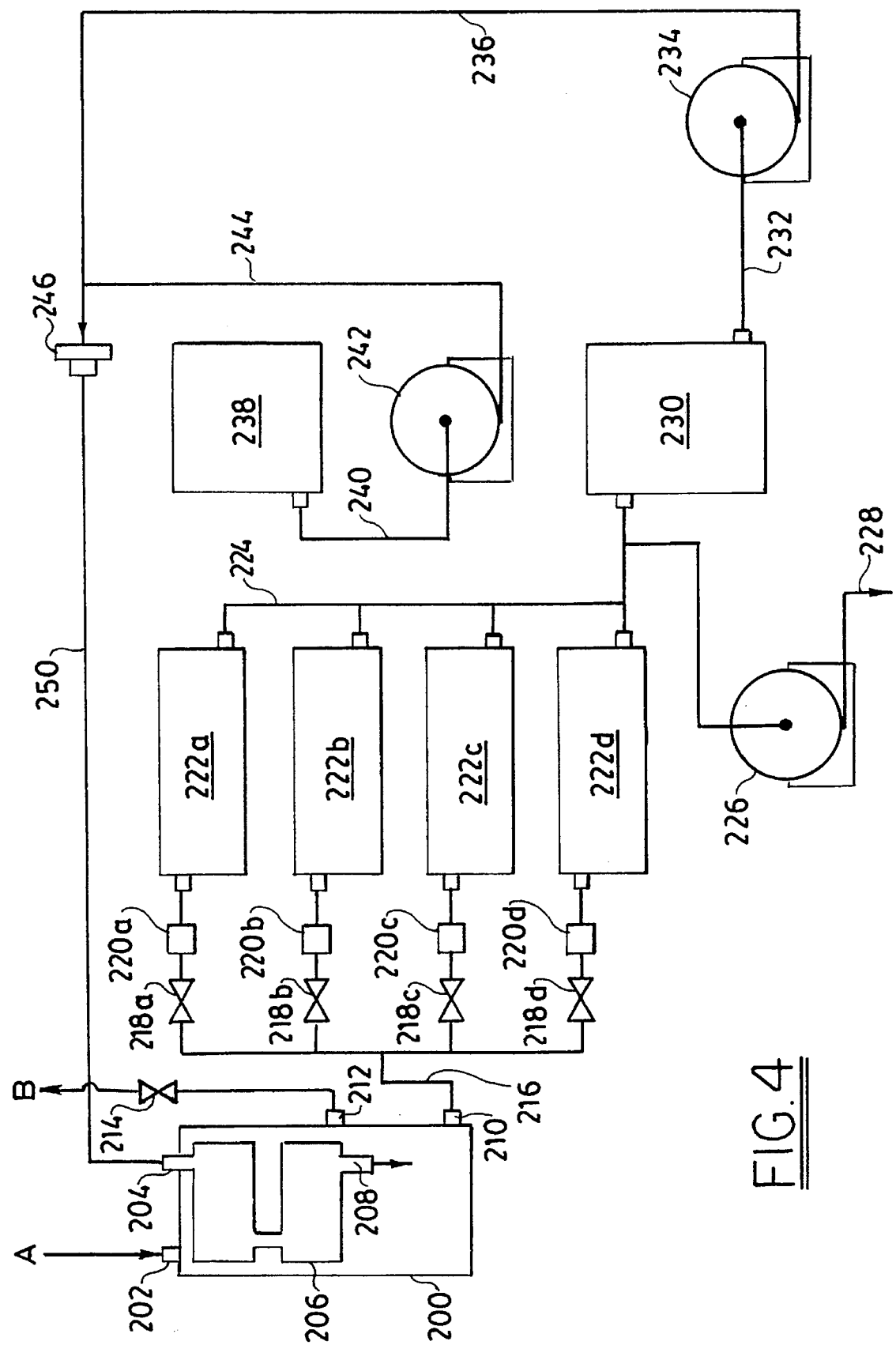
FIG. 4 is a schematic view of a second embodiment of the system of the present invention.

FIG. 4 is a schematic view of a second embodiment of the in vitro system of the present invention. In this system, cell culture medium is contacted with oxygen-containing gas A within gasification chamber 200. Carbon dioxide-containing cell culture medium enters gasification chamber 200 through inlet 204 and contacts membrane 206 which spreads the medium and promotes better contact between it and oxygen-containing gas A entering through inlet 202. Inlet 202 includes a sensor (not shown) to monitor the amount of carbon dioxide in gas A at that location. A carbon dioxide level of 4 to 5% is needed to buffer the cell culture medium to a proper pH. Membrane 206 can be constructed from a variety of suitable gas-liquid contact materials such as a polytetrafluoroethylene screen. After such contact, oxygen-containing culture medium is discharged from gasification chamber 200 by way of spout 208, outlet 210, and oxygenated medium conduit 216. Carbon dioxide-containing gas B, which is desorbed from the culture medium in gasification chamber 200, is discharged by way of exhaust gas outlet 212. Control valve 214 maintains the pressure of gasification chamber 200 at a suitable level (i.e. 17–20 psia).

Oxygenated culture medium in conduit 216 is charged through valves 218a–d and flow meters 220a–d to cell culture chambers 222a–d, respectively. No pump is needed to convey material from gasification chamber 200 to cell culture chambers 222a–d, because the gasification chamber is maintained at an elevated pressure which forces the culture medium into cell culture chambers 222a–d. Valves 218a–d are used to adjust the flow rate of culture medium into each of cell culture chambers 222–d. These valves may be controlled manually or by conventional flow control techniques which are well known in the art. Flow meters 220a–d can be in the form of rotameters which display the flow rate of material to each of the cell culture. chambers.

Effluent cell culture medium from chambers 222a–d passes through spent medium conduit 224 either to spent medium pump 226 or collection chamber 230. Spent medium pump 226 conveys medium to collection site 228. Medium within collection chamber 230 is drawn through conduit 232 by pump 234 and discharged through conduit 236. The volumetric flow rate with which medium is withdrawn by pump 234 from collection chamber 230 is variable depending upon the level of medium in chamber 230.

Medium in conduit 236 is supplemented with fresh medium from conduit 244. Such fresh medium is stored in reservoir 238 and withdrawn through conduit 240 by pump 242. The blend of spent medium in conduit 236 and fresh medium in conduit 244 passes through filter 246 and conduit 250 before reentering gasification chamber 200 at inlet 204. Filter 246 removes dead cells and debris.

In essence, the addition of fresh medium from reservoir 238 coupled with the removal of spent medium to collection site 228 simulates the excretion of waste material and experimental additives by the kidneys. In steady state operation, medium discharged to collection. site 228 should substantially equal that provided from fresh medium reservoir 238.

FIG. 5 is a detailed perspective view of the second embodiment (see FIG. 4) of the in vitro system of the present invention. This figure shows gasification chamber 200, oxygenated medium conduit 216, valves 218a–d, flow meters 220a–d, cell culture chambers 222a–d, collection chamber 230, pump 234, fresh medium reservoir 238, conduit 240, and pump 242. As shown, valves 218a–d, rotameters 220a–d, cell culture chambers 222a–d, and pumps 234 and 242 are all mounted to rack 251. Collection chamber 230 and fresh medium reservoir 238 rest on rack 251, while gasification chamber 200 is adjacent. Pumps 234 and 242 are cassette pumping units made by Manostat, New York, N.Y. Each pump has its own motor with a gear box and a drive shaft extending through rack 251, thereby mounting the pumps to the rack.

Figure 6:
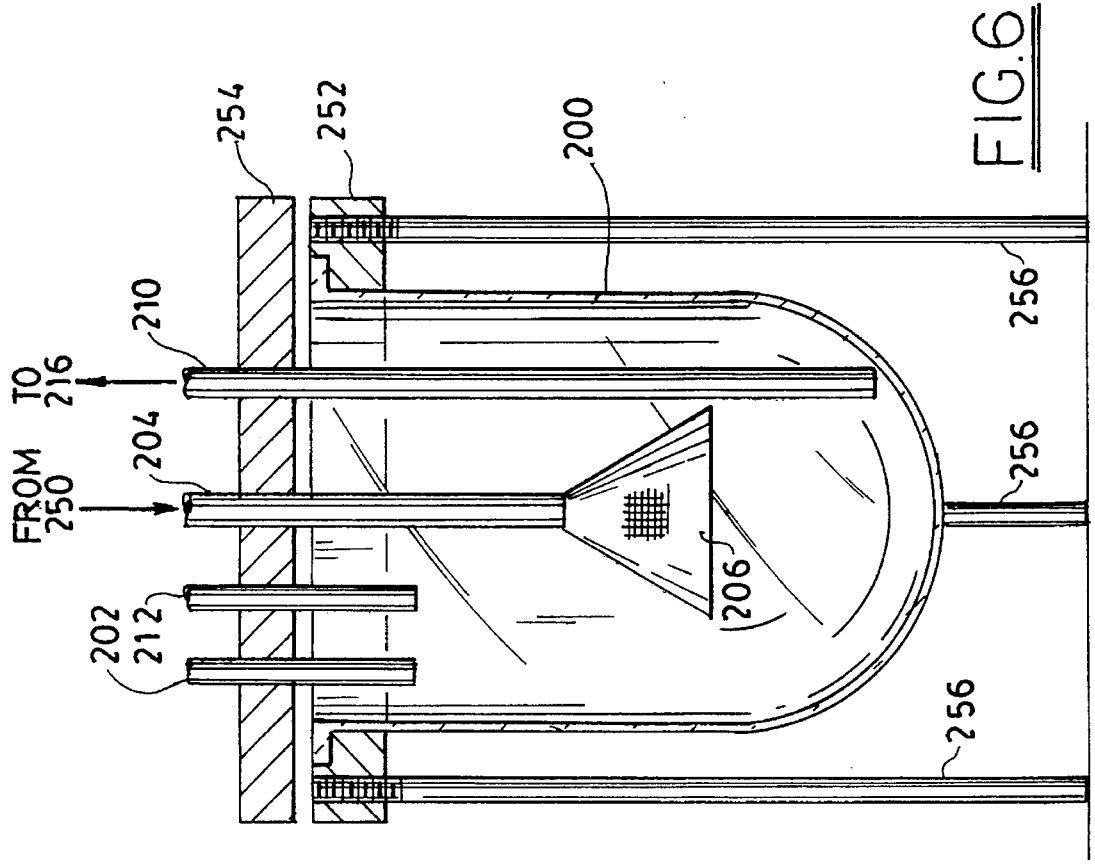
FIG. 6 is a perspective view of the gas-liquid exchange device of FIG. 5.

FIG. 6 is a perspective view of gasification chamber 200 of FIG. 5. Gasification chamber 200 is suspended from support ring 252 which is supported by legs 256. Fitted over support ring 252 is flange 254 having ports to accommodate a plurality of conduits. These conduits include oxygen-containing gas inlet 202, carbon dioxide-containing cell culture medium inlet 204 from conduit 250, oxygenated medium outlet 210, and exhaust gas outlet 212. Positioned on the end of inlet 204 is gas exchange membrane 206. Oxygenated medium outlet 210 extends into gasification chamber 200 in order to withdraw oxygenated cell culture medium. Flange 254 of gasification chamber 200 also is provided with additional ports (not shown) either to withdraw gas or liquid samples, to introduce solid, gaseous, or liquid test compounds, or to take measurements of parameters such as pH, temperature, etc.

Figure 7:
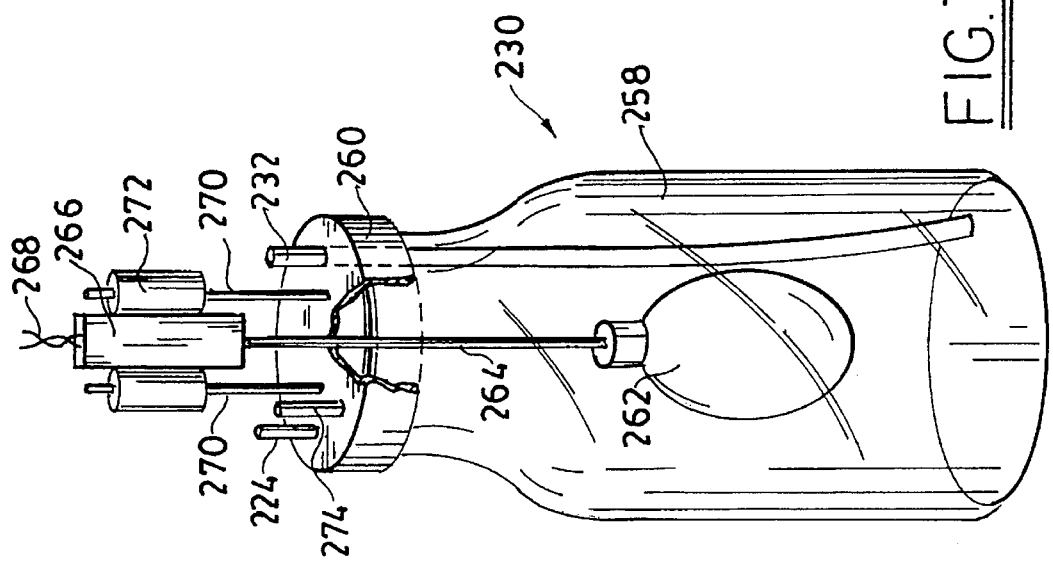
FIG. 7 is a perspective view of the medium reservoir of FIG. 5.

FIG. 7 is a perspective view of cell culture medium reservoir 230 of FIG. 5. This chamber includes container 258 on which cover 260 is fitted. Cover 260 is provided with a plurality of ports to receive fluid conduits and other structure. These ports receive spent culture medium conduit 224 from cell culture chambers 222a–d, discharge conduit 232 which leads to pump 234, and waste gas conduit 274 which is connected to exhaust gas outlet 212 of gasification chamber to maintain a positive pressure within chamber 230. Conduit 232 extends into container 258 in order to withdraw medium from collection chamber 230. Also extending through cover 260 is arm 264 which is connected to glass float 262. Arm 264 is also fixed to linear potentiometer 266 which is supported by mounting unit 272 that is supported on cover 260 by legs 270. Electrical connector 268 is connected to a control mechanism (not shown) for pump 234. As the level of culture medium in container 258 increases, float 262 moves upwardly, causing linear potentiometer 266 to send a signal through electrical connector 268 to the actuator for pump 234, causing that pump to increase the rate at which medium is withdrawn from collection chamber 230.

Figure 8:
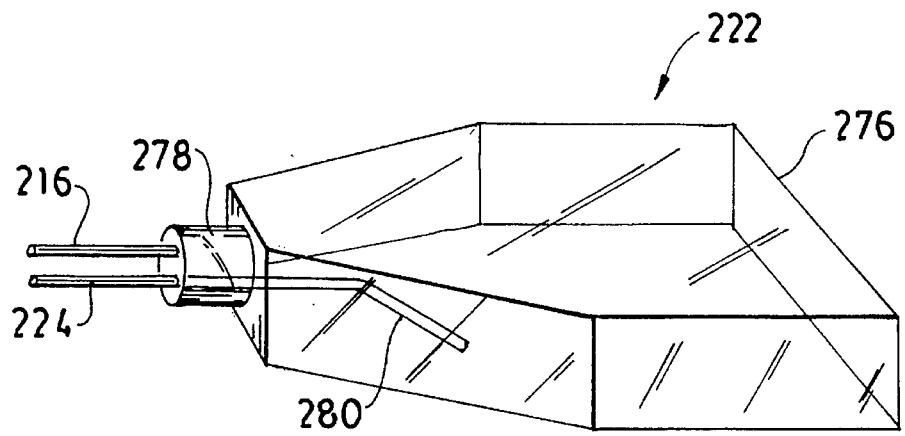
FIG. 8 is a perspective view of a cell culture chamber of FIG. 5.

FIG. 8 is a perspective view of a cell culture chamber 222 of FIG. 5. Cell culture chambers 222a–d are typically in the form of standard polystyrene tissue culture flasks in which tissue culture cells typically grow. Each chamber contains a cell type of the organ it is intended to simulate. Cell culture chamber 222 includes clear container 276 having an opening with an inlet cap 278. Extending into inlet cap 278 is oxygenated medium conduit 216, while spent culture medium conduits 224 extends through cap 278 and into the interior of container 276. To facilitate withdrawal of medium from container 276, conduit 224 is provided with dip tube 280 which will extend below the level of medium in the chamber. In some embodiments it may be desirable to include glass or polymeric beads within chamber 276 to support and grow cells. In some embodiments the form of the cell culture chambers may be altered to facilitate the culture of cells on glass or polymeric beads.

Figure 9:
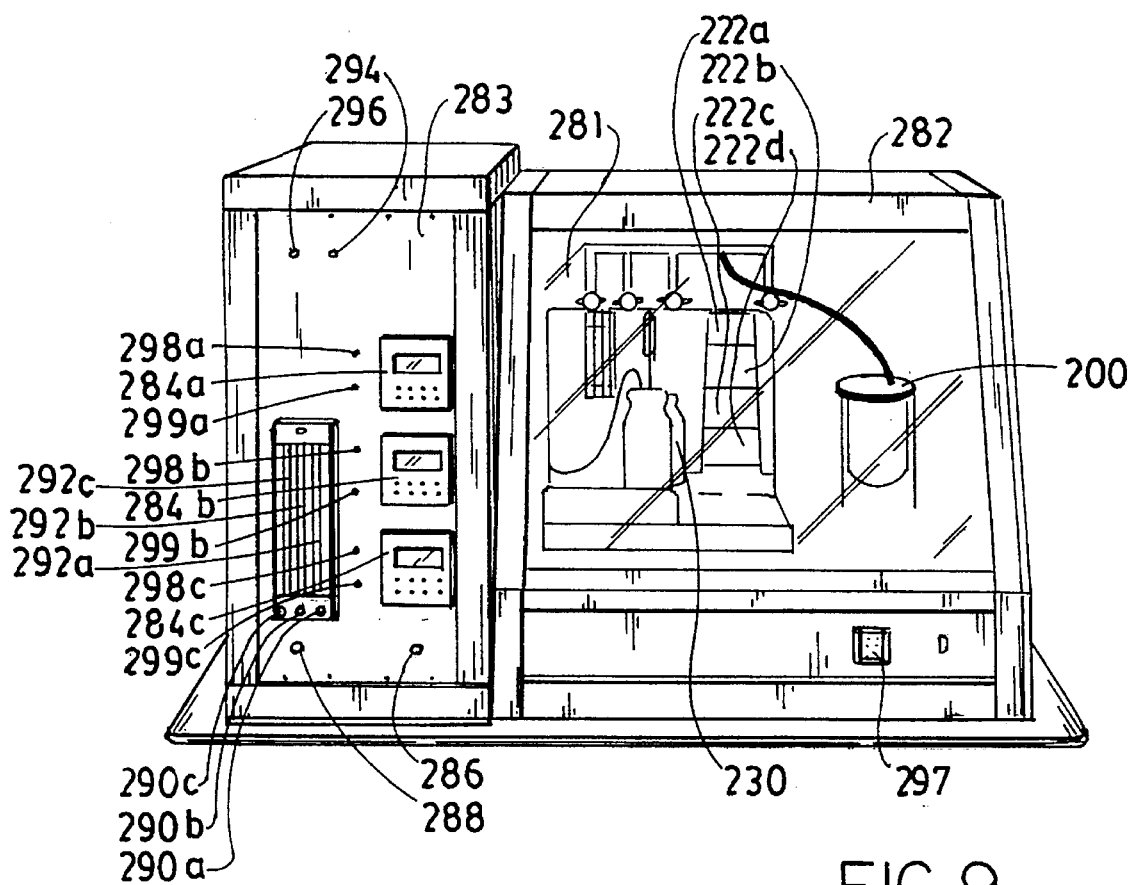
FIG. 9 is a perspective view of the system of FIG. 5 in a cabinet.

FIG. 9 is a perspective view of the in vitro system of FIG. 5 in a cabinet. This figure depicts the components of FIG. 5, including gasification chamber 200, cell culture chambers 222a–d, and collection chamber 230 within cabinet 282 having cover 281. The exterior panel 283 of cabinet 282 includes a plurality of digital read-out indicator/controller displays 284a–c with indicator controller 284a being utilized for pH control, indicator/controller 284b being utilized to control dissolved oxygen, and indicator/controller 284c being utilized to monitor the temperature within the system. Kidney function potentiometer 286 sets the kidney function rate by controlling the speed of pump 242. Scavenger pump control potentiometer 288 is utilized to set the level of cell culture medium in collection chamber 230 by controlling the rate with which pump 234 withdraws material. Panel 283 also includes power switch 294 and power indicator lamp 296. Temperature controller 297 regulates the temperature within cabinet 282. High indicator lamps 298a–c and low indicator lamps 299a–c are also present on panel 283 to advise the operator when the magnitude of certain parameters is outside preselected values. High indicator lamp 298a and low indicator lamp 299a are directed to pH indication. High indicator lamp 298b and low indicator lamp 299b are directed to dissolved oxygen indication. High indicator lamp 298c and low indicator lamp 299c are utilized to indicate the temperature of the cell culture medium.

The composition of oxygen-containing gas supplied to the system is controlled with needle valves 290a–c with valve 290a being for oxygen control, valve 290b being for nitrogen control, and valve 290c being for carbon dioxide control. Gas rotameters 292a–c indicate the amount of oxygen, nitrogen, and carbon dioxide, respectively, which are provided to the system in the oxygen-containing gas. Typically, this gas contains 0 to 8%, preferably 4–5%, carbon dioxide, 5 to 15%, preferably 15%, oxygen, and 70 to 95%, preferably 80%, nitrogen.

Figure 10:
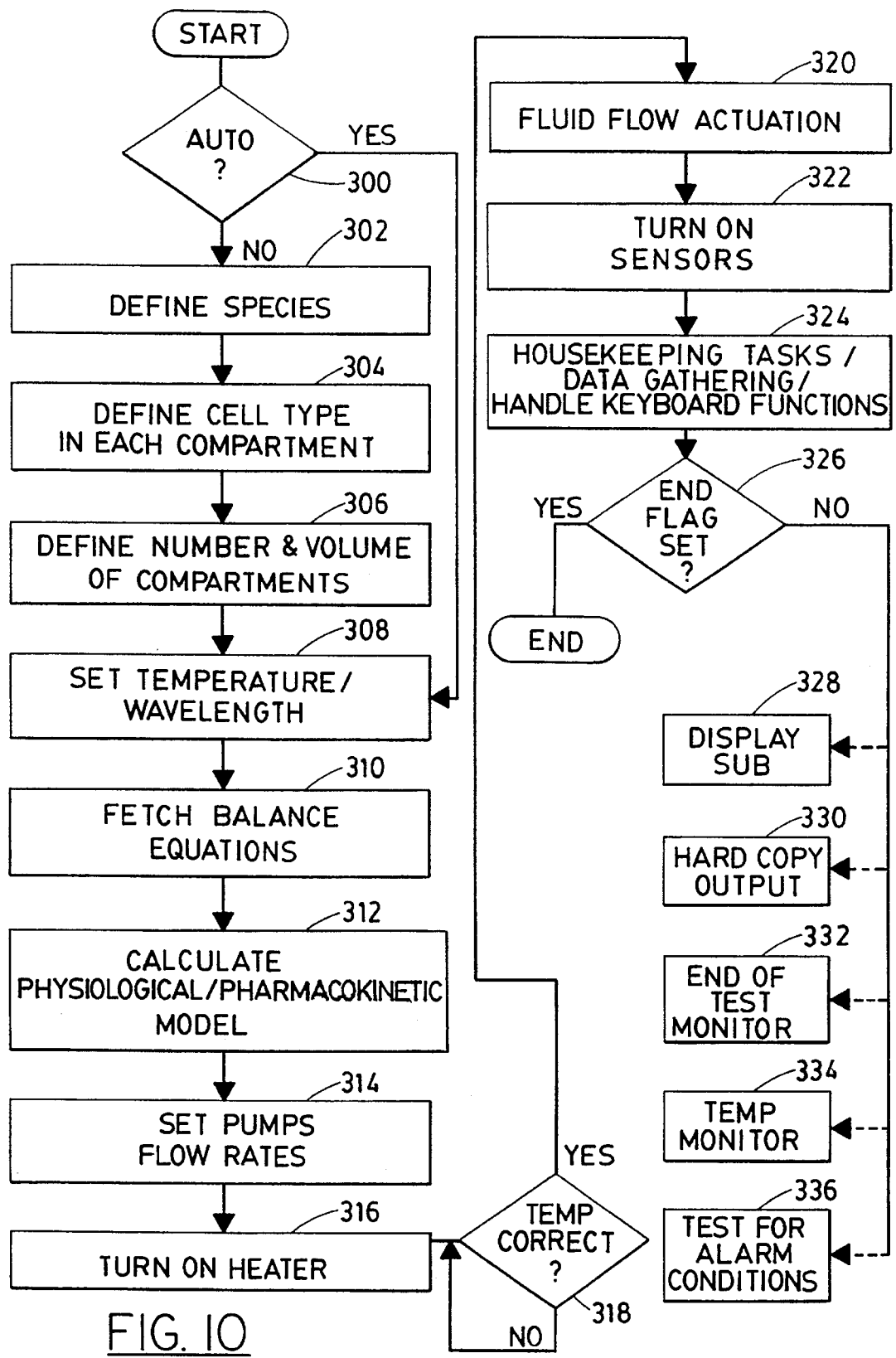
FIG. 10 is a block diagram for a microprocessor control of the system of the present invention.

FIG. 10 is a block diagram for microprocessor control of the in vitro system of the present invention, such as that shown in FIG. 3. As shown in FIG. 10, the computer software initially enters decision block 300 to determine whether the system is configured to proceed in an automatic mode where the cell culture chambers are constructed as electrically "intelligent" compartments (discussed supra with reference to FIG. 16) or in a semi-automatic mode. In the semi-automatic mode, the program proceeds via blocks 302, 304, 306, and 308 to receive operational instructions entered through keyboard 104 (FIG. 3) to define the species which the system models (block 302), the cell type in each compartment (block 304), the number and volume of cellular compartments (block 306), and the temperature and/or wavelength at which the experiment is to be carried out (block 308).

At block 310, one or more material balance equations which are needed to model the experiment are obtained from look-up table 110 based on the species model, cell type, number and volume of cellular compartments, etc. The program then proceeds to block 312 to calculate a physiologically-based pharmacokinetic model for the chemical being tested. Next, the program proceeds to block 314 which causes input/output interface 100 of microprocessor 98 (see FIG. 3) to output physiologically-based pump settings which determine the fluid flow rates for various cell compartments.

Heater 90 is turned on at block 316. The software then proceeds to decision block 318 which monitors the output of temperature probe 92 to ensure that culture medium circulation begins only after the medium in reservoir 50 has reached an appropriate temperature.

Once the proper temperature has been established, the program proceeds to block 320 which actuates valves 64 and 80 through control lines (not shown in FIG. 3) to initiate the flow of culture medium to chambers 56 and 68. The program next proceeds to block 322 which commands sensors 60 and 72 for monitoring the biological activity of the system through control lines 124a–c.

The program then proceeds to block 324 where general housekeeping tasks are carried out. These include test data gathering, storing, and displaying.

Periodically, in response to hardware or software generated interrupts, the program proceeds to decision block 326 to determine whether an end-of-test flag (described infra) has been set. If so the program proceeds to its defined "test end". Otherwise, the program sequentially proceeds through display subroutine 328 (FIG. 12), hard copy output subroutine 330 (FIG. 13), end of test monitor subroutine 332 (FIG. 14), temperature monitor subroutine 334 (FIG. 11), and test for alarm conditions subroutine 336 (FIG. 15).

Figure 11:
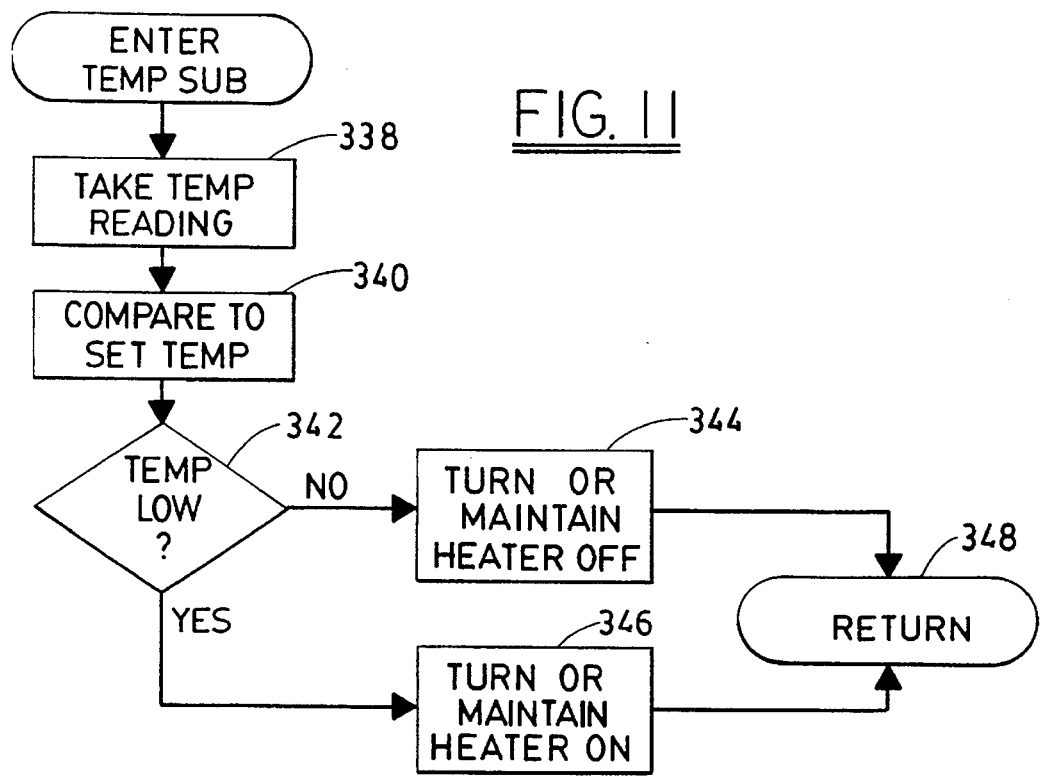
FIG. 11 is a block diagram of a temperature monitoring subroutine for the present invention.

FIG. 11 is a block diagram of a temperature monitoring subroutine which can be used in conjunction with the block diagram of FIG. 10. Upon entry into this subroutine, block 338 takes a temperature reading off of probe 92, compares the measured temperature to an internally-stored desired temperature at block 340, and determines whether the appropriate temperature has been reached at decision block 342. If the temperature is above the desired value, heater 90 is turned off in block 344. Otherwise, heater 90 is either turned on or kept turned on at block 346. The software is then returned to the main software program of FIG. 10 by return block 348.

Figures 12, 13:
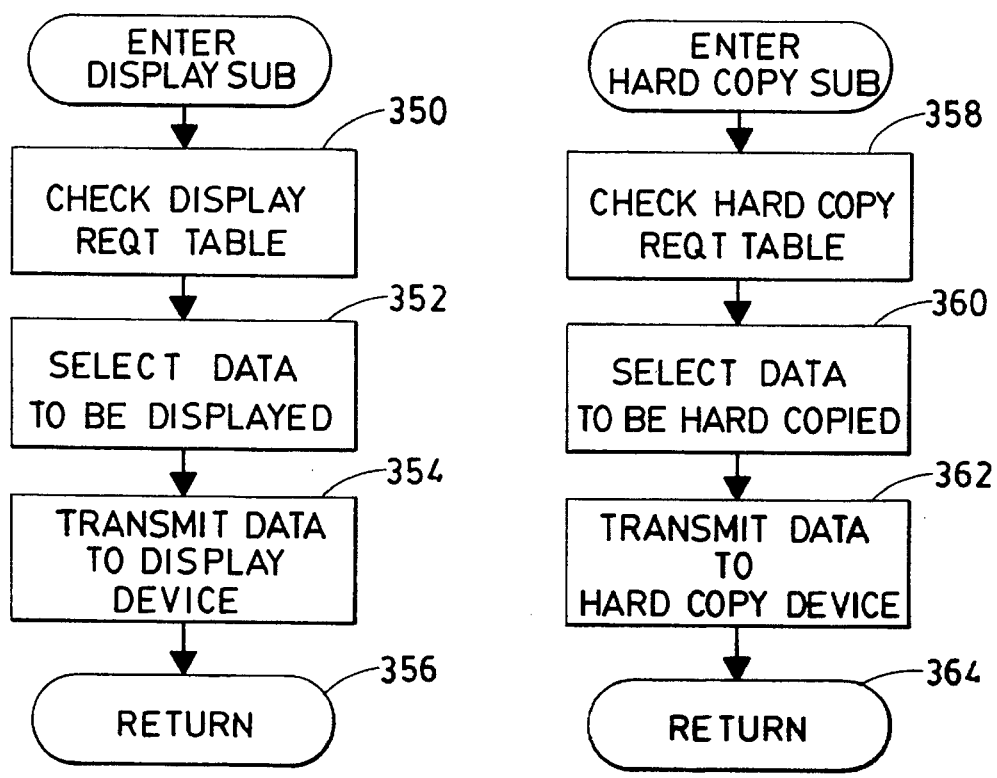
FIG. 12 is a block diagram of a display subroutine for the present invention.
FIG. 13 is a block diagram of a hard copy subroutine for the present invention.

FIG. 12 is a block diagram of a display subroutine for use in conjunction with the block diagram of FIG. 10. In this subroutine, the program enters block 350 where an internally maintained display request table is consulted to check for predetermined or operator-requested quantities/parameters/test results to be displayed on display 114. Based on this information, the program, at block 352, selects the data to be displayed and organizes it in a format suitable for transmission to display 114. This data is transmitted at block 354 to display 114, and the program is then returned by return block 356 to the main block diagram program of FIG. 10.

FIG. 13 is a block diagram of a hard copy subroutine suitable for use in conjunction with the block diagram of FIG. 10. In this subroutine, block 358 consults an internally-maintained display request table to check for predetermined or operator-requested quantities/parameter/test results that are to be displayed in hard copy by printer/plotter recorder 112. Based on this criterion, block 360 of the subroutine selects appropriate quantities and parameters to be recorded and organizes them in a suitable format for transmission to recorder 112. After such transmission by block 262, the program returns to the main program of FIG. 10 through return block 364.

Figure 14:
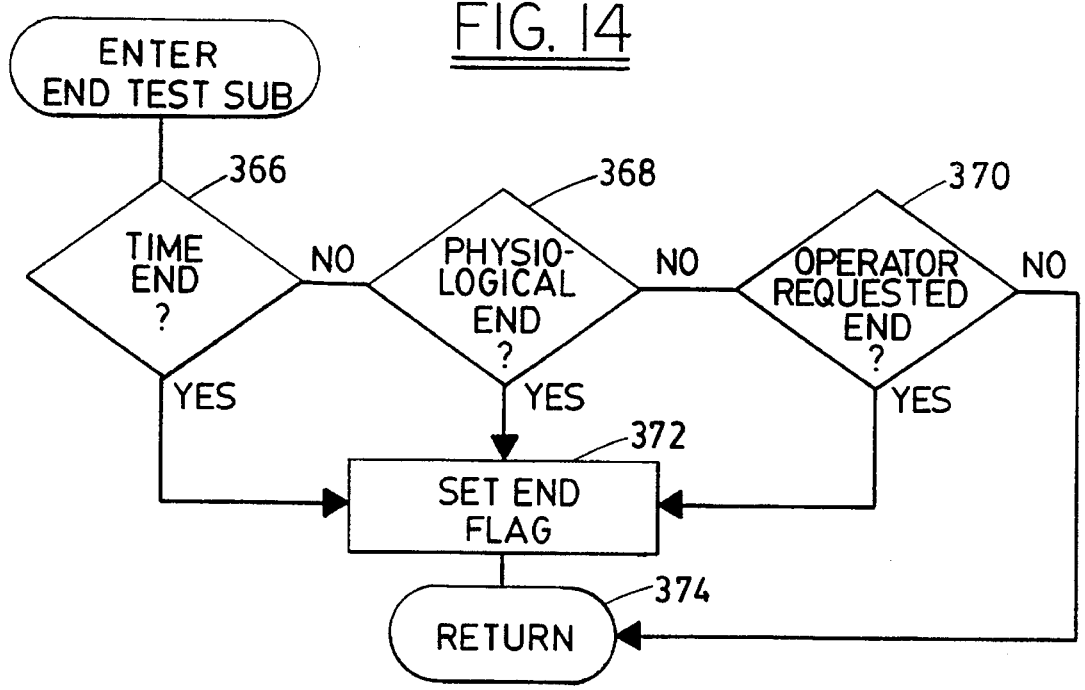
FIG. 14 is a block diagram for an end of test subroutine for the present invention.
Figure 15:
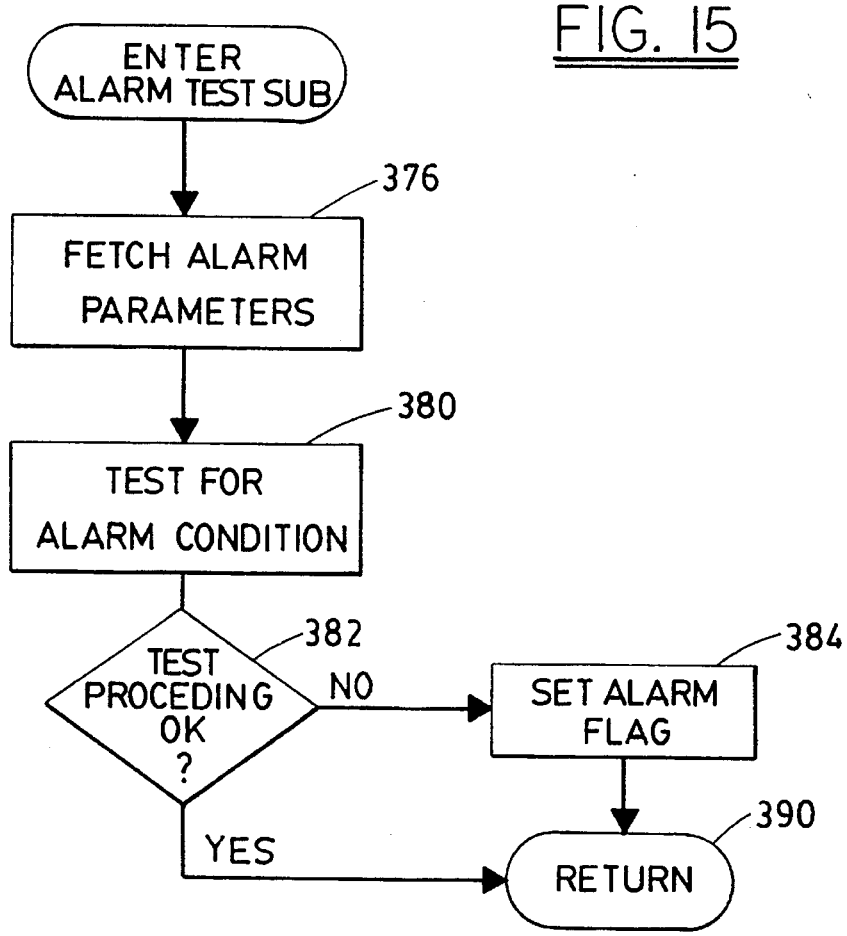
FIG. 15 is a block diagram for an alarm subroutine for the present invention.

FIG. 14 is a block diagram for an end-of-test subroutine useful in conjunction with the block diagram program of FIG. 10. In this subroutine, decision block 366 is entered to determine whether the program has been running for a predetermined time period. If not, decision block 368 is entered, and the end-of-test condition is determined based on whether certain test results (e.g., quantity of cancerous cells, toxicity level, etc.) has been achieved. If not, decision block 370 examines whether an end-of-test signal has been requested from keyboard 104. If not, the subroutine returns to the program of FIG. 10 through return block 374. Alternatively, if the result of any of decision blocks 366, 368, or 370 is affirmative, an "end-of-test" flag is set at block 372. The subroutine then proceeds back to the main block diagram program of FIG. 10 through return block 374.

FIG. 15 is a block diagram for an alarm subroutine useful in conjunction with the block diagram of FIG. 10. This is responsible for outputting visual or audible alarms should the program detect that the experiment being conducted is not proceeding properly. For example, the test results are not falling within an expected range profile. This subroutine first proceeds to block 376 where stored alarm conditions are retrieved from a memory. The program then proceeds to block 380 at which dynamically-obtained test progress results are compared to the retrieval alarm conditions. Decision block 382 then analyzes whether the test results are within the expected ranges. If not, an alarm is set to actuate visual or audible indications at block 384. The subroutine then returns to the main program of FIG. 10 through return block 390. If the result of decision block 382 is affirmative, the subroutine proceeds directly to return block 390.

The system of the present invention is accordingly designed to allow cell forms, of humans or other species, to be exposed to a test chemical in a manner consistent with in vivo exposure. In order to perform this function, the system incorporates several features. First, the compartments in which the biological cells reside are constructed to be mathematically equivalent to the volume of distribution (physical size) of the organ or tissue being modeled. For example, the compartment for the hepatocyte culture would represent the volume of distribution for the liver.

Second, the flow rates between the various compartments are biologically based to represent correctly the flow rates between and among the corresponding biological organs, tissue, etc. In this way, cells residing in the compartments are exposed to concentration of test materials in a manner consistent with human or animal exposure to the test material. Additionally, metabolites of one cell type, which may be affected by the presence of the test material, or metabolites of the test material, can be exchanged among the biological cells in the compartments.

The system of FIG. 3 constitutes a microprocessor controlled instrument that performs the functions of exposing the biological cells of different tissue origin to test material at a rate modeling a selected species. Species modeling and flow control are performed by the microprocessor which serves as the overall controller so that it carefully controls flow rates, temperature, and other conditions within the system to mimic, as closely as possible, conditions within the human or other species being modeled.

The present invention permits with appropriate inputs to model, among other things, the numbers of compartments, the volume of compartments, cell type, etc. The microprocessor is able to configure the correct model for a given problem with a database of physiological organ flow rates obtained from general reference information for each species.

Since the system of the present invention is interactive (i.e., the computer not only senses but also controls the conditions within the test), corrections can be dynamically instituted into the system and appropriately noted and documented for apprising researchers of the dynamics of the test being run.

Data gathering by the computer consists of the collection of data required for continuous in-line monitoring of test chemical effluent from each compartment. Sensors 60 and 72, preferably of the flow-through type, are disposed in-line with the outflow from each compartment, to thus detect, analyze and provide quantitative data regarding the test chemical effluent from each compartment.

Microprocessor 98 may also serve to compute a physiologically-based pharmacokinetic (PBPK) model for a particular test chemical. These calculations may serve as the basis for setting the flow rates among compartments and excretion rates for the test chemical from the system. However, they may also serve as a theoretical estimate for the test chemical.

At the conclusion of the experiment, predictions concerning the concentrations of test chemicals and metabolites made by the PBPK determination can be compared to the sensor data. Hard copy output compares the PBPK model with experimental results.

Figure 16:
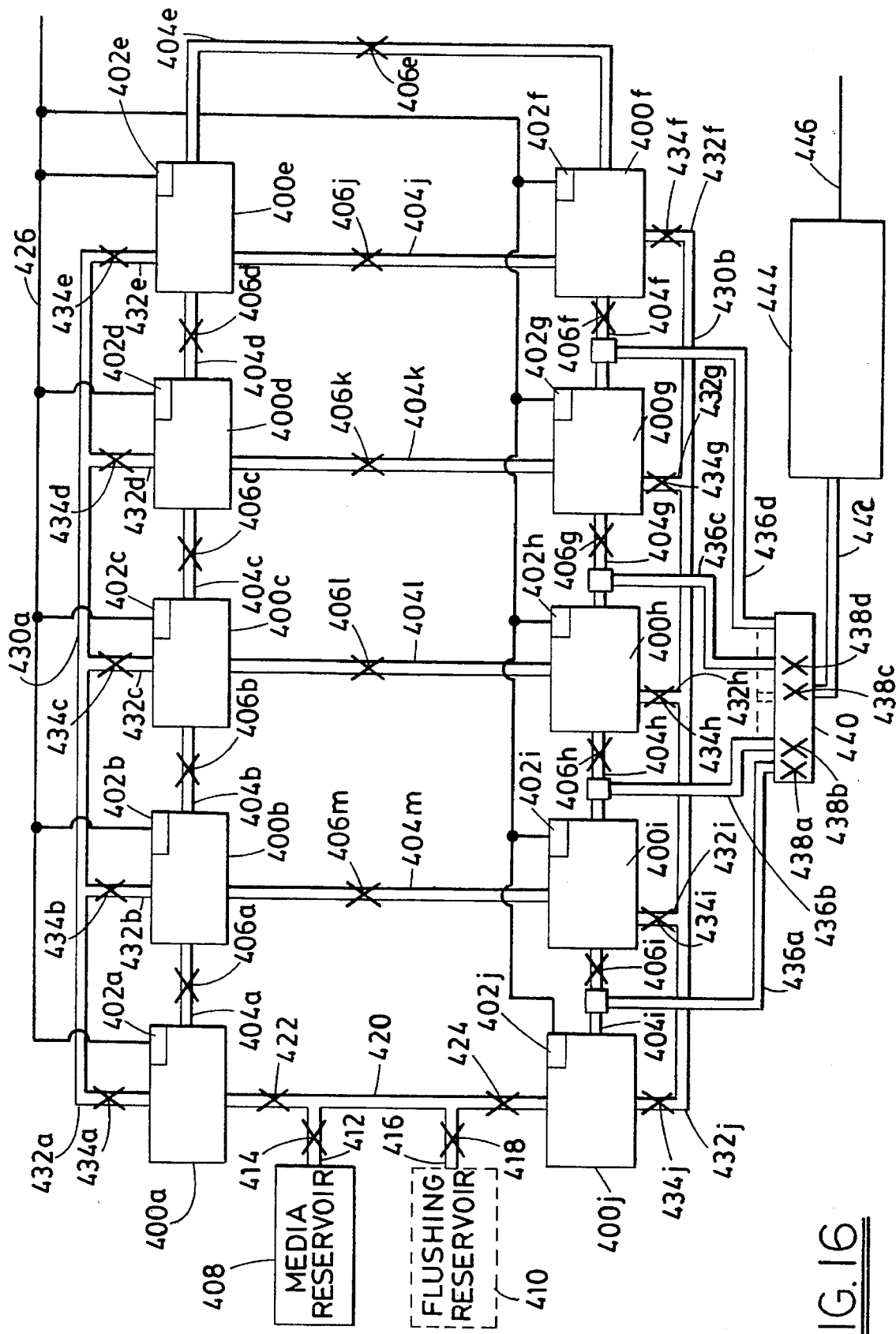
FIG. 16 is a schematic view of a third embodiment of the system of the present invention.

FIG. 16 is a schematic drawing of a third embodiment of the system of the present invention. It illustrates a complex of conduits connecting a large number of cell culture chambers 400a–j. Each of these chambers includes an "intelligent" module 402a–j which holds characterizing information readable by a microprocessor via data bus 426. Modules 402a–j define for a given chamber its cell type, the species to be modeled, etc. which is stored in an on-board, non-volatile memory, in a bank of switches, or in any other form used for data storage.

Cell culture chambers 400a–j are connected with one another through conduits 404a–m having valves 406a–m and connection manifolds 430a–b which are in communication with conduits 432a–j having valves 434a–j. This conduit system is coupled to media reservoir 408 by means of conduit 412 having valve 414 and conduit 420 having valves 422 and 424. Flushing reservoir 410 also communicates with conduit 420 by means of conduit 416 having valve 418.

This system is also provided with sample conduits 436a–d having valves 438a–d within valve network 440. As a result selected samples can be taken at locations between cell culture chambers 400f–j. Similarly, samples can be taken between cell culture chambers 400a–e. The selected sample is carried by conduit 442 to sensor 444. The values measured within sensor 444 are carried to a main microprocessor (not shown) via control line 446.

Using the system of FIG. 16, a large number of different test set-ups can be arranged so that test chemical injected into the system through media reservoir 408 can flow through a path of selected cell culture chambers 400a–j. It is also possible to establish two parallel and independent circulation paths for use in simultaneously analyzing the efficacy of a given test chemical on different cell cultures.

Flushing reservoir 410 holds a flushing solution for pumping through the entire system to remove any residues from prior tests. If desired, the above-described conduits 404a–m, 430a–b, 432a–j are provided, respectively, with valves 406a–m and 434a–j if necessary.

EXAMPLES

EXAMPLE 1

Simultaneous Exposure of Normal and Transformed Cells to an Antineoplastic Compound in a Multicompartmental Cell Culture System Chemicals All chemicals were purchased from Sigma Chemical Company (St. Louis, Mo.) unless otherwise stated and were of the highest purity available.

Cell Cultures

Approximately 14 mL of freshly drawn human blood were collected into EDTA tubes (Becton Dickinson, Lincoln Park, N.J.). To this blood sample was added 4 mL of Hanks balanced salt solution. Two and one-half mL of the blood solution was layered onto 3 mL of ficoll (Pharmacia, Piscataway, N.J.) and centrifuged at 1500 rpm for 20 min at ambient temperature. The pellet was washed in an equal volume of Hanks balanced salt solution and recentrifuged. All lymphocytes collected from the 14 mL blood sample were seeded into 100 mL of RPMI 1640 (Gibco, Grand Island, N.Y.) and placed in a Forma Scientific water-jacketed incubator (Fisher Scientific, Philadelphia, Pa.) set at 37° C. with 5 percent $CO_2$ overnight.

A rat hepatoma cell line, H4IIE obtained from the American Type Culture Collection (Bethesda, Md.), was cultured in RPMI Medium 1640 with 5 percent fetal calf serum, L-glutamine and antibiotics (penicillin G, streptomycin and amphotericin B) (Gibco Island, N.Y.). Cells were seeded 24 hr before the experiment. Attachment of H4IIE cells occurs several hours following seeding. Density was approximately 20 percent of confluence at the start of the experiment.

Multicompartmental Cell Culture System

The multicompartmental cell culture system ("MCCS") of the present invention was used to expose both normal and transformed cells to an antineoplastic compound simultaneously. The volume of distribution of the system was 500 mL. Each compartment (T-flask, Becton Dickinson, Lincoln Park, N.J.) contained 75 mL of cell culture medium (RPMI 1640 as previously described). The flow rate was set at 5 mL per min. and maintained by means of a peristaltic pump (Millipore, Bedford, Mass.). The entire system was placed inside a Forma Scientific water-jacketed incubator (Fisher Scientific, Philadelphia, Pa.) set at 37° C. with 5 percent $CO_2$.

Treatment of Cells

One hour after connecting the compartments, the MCCS was treated with 5-bromo-2'-deoxyuridine ("BrdU") by injecting 1 mL of dimethylsulfoxide containing 750 mg of BrdU into a reservoir. The system was allowed to run for 24 hr. Separate T-flasks containing untreated lymphocytes and hepatoma cells were incubated concurrently as total viability controls.

Following the 24 hr. exposure period, both human lymphocytes and rat hepatoma cells were exposed to a UV light source for 30 sec. Viable cells were determined and enumerated by trypan blue dye exclusion on a hemacytometer immediately following UV exposure.

Results

Figure 17:
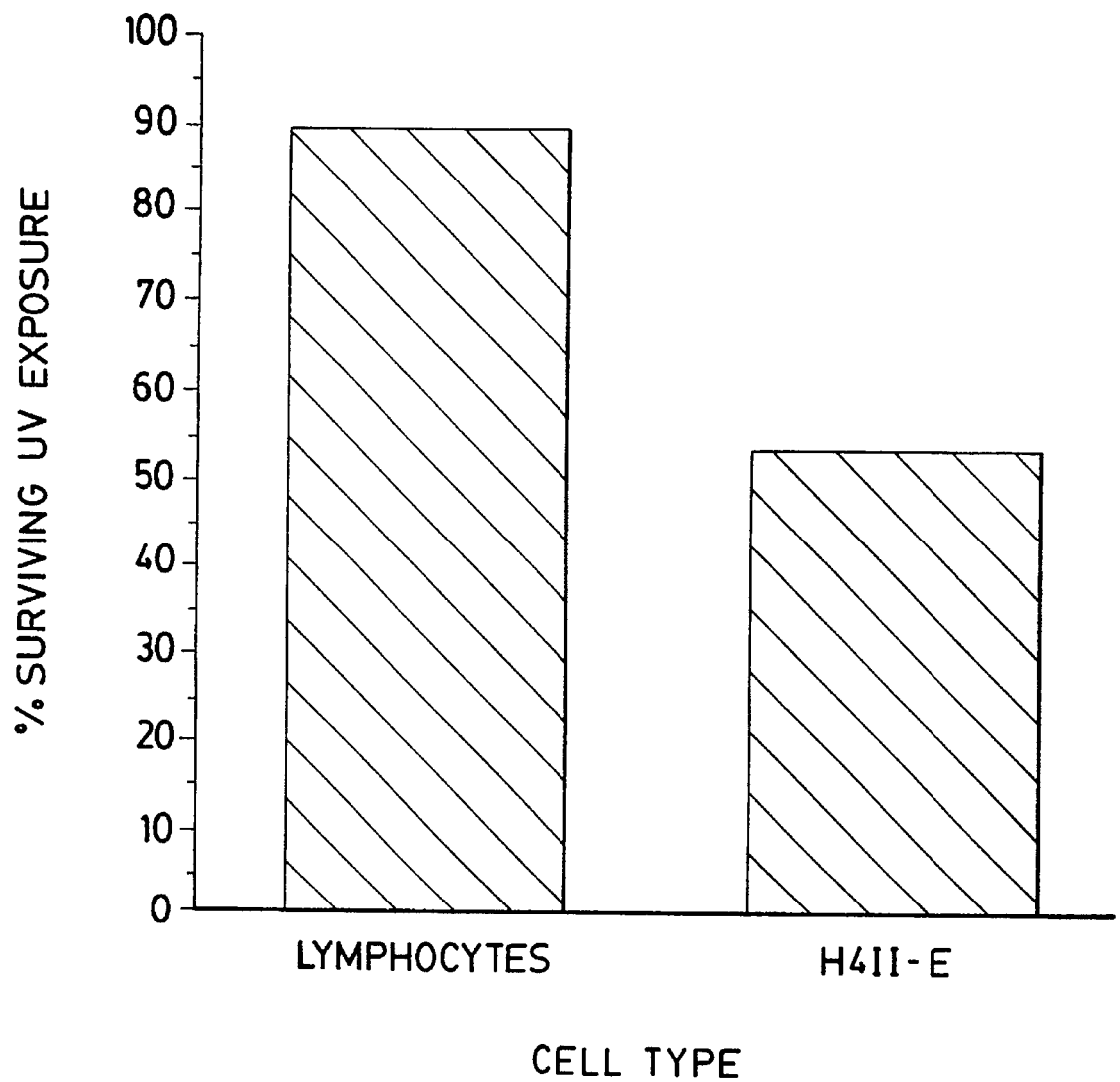
FIG. 17 is a bar graph depicting the viability of human lymphocytes and H4IIE cells following 24 hr exposure to BrdU and 30 sec exposure to UV light.

Eighty-nine percent of the human lymphocytes survived the UV exposure, while only fifty-three percent of the H4IIE cells were viable following UV exposure (FIG. 17). This enhanced killing was due to greater uptake of the BrdU by the hepatoma cells than the lymphocytes. This was to be expected, since BrdU is incorporated into the DNA of cells during DNA synthesis, and the rate of DNA synthesis of transformed cells such as the H4IIE cells is much greater than the rate of DNA synthesis of nontransformed, slowly dividing cells such as the lymphocytes.

These results indicate that it is possible to expose different cell types in the MCCS to a test agent and demonstrate differential uptake of the agent in the device. Additionally, since the BrdU serves as a model for the common metabolite uridine, the experiment supports the use of the MCCs to allow different cell types to exchange metabolites. Furthermore, by altering the flow rates on the pumping device or including individual pumps for each chamber, kinetic modeling of the system is easily performed.

A practical use for the MCCS is to provide a device in which several cell types may be exposed to a test chemical simultaneously in order to determine differential toxicity of the test chemical to the cells.

Illustratively, methods such as the following can be employed to identify potential antineoplastic agents that are effective against transformed cells, but have low toxicity to normal.

Additionally, such methods as the following can be used to describe the kinetics of a drug or test chemical in the MCCS.

EXAMPLE 2

Physiologically-Based Pharmacokinetic Model for Naphthalene

To model the metabolism of a living organism, the MCCS system can be modified to account for the expected metabolic functions. In order to do this, it is necessary to thoroughly understand the metabolism of certain cell types and compounds. The following example using naphthalene, describes how to work out the equations necessary to set up a physiologically-based pharmacokinetic (PBPK) model. Once these equations have been derived and tested, then the MCCS system would be set up with the required measuring devices such as probes and spectrophotometers to monitor the metabolism of the system. To control the metabolism of the system, additional reservoirs would be added in order to maintain or adjust the gas mixture, acidity, and to add various compounds or metabolites are required to model completely a physiologically-based system. The entire set-up would be controlled by a microprocessor programmed to account for both the metabolic equations and to adjust the various parameters in order to maintain closely a metabolic model of a human or animal system.

Figure 18:
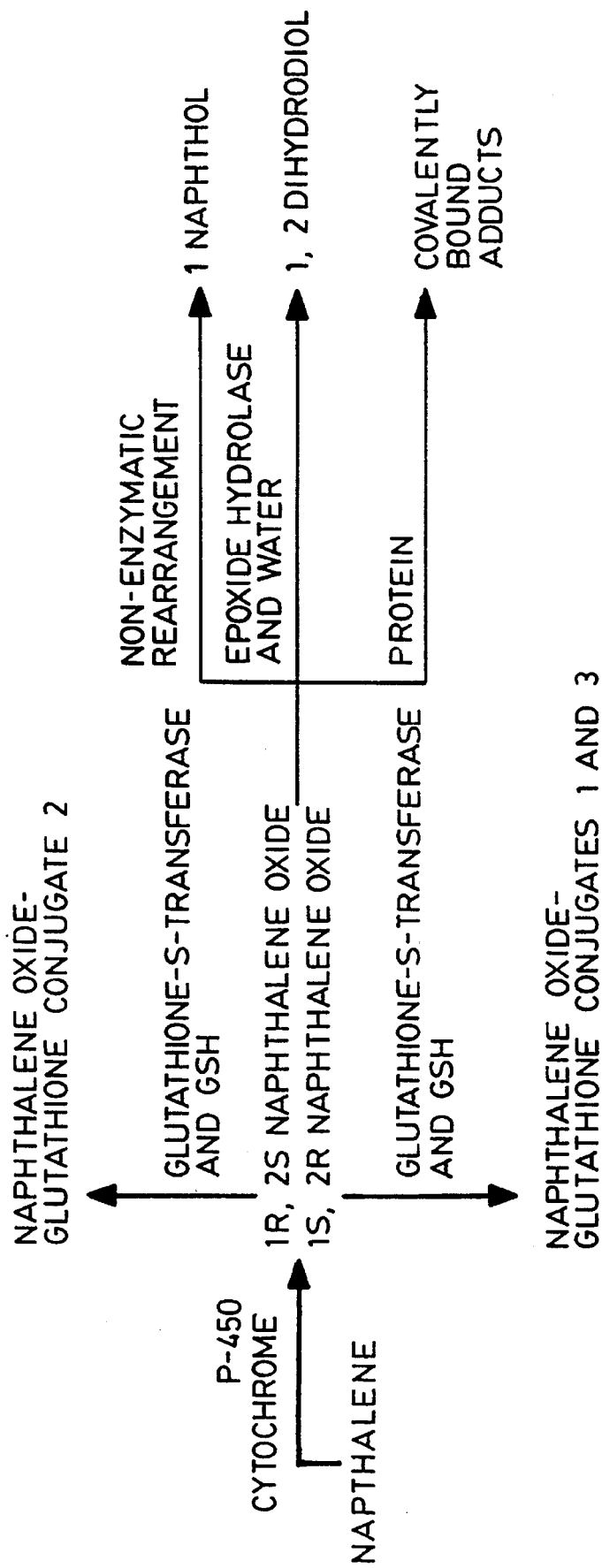
FIG. 18 is a schematic diagram of the biotransformation of naphthalene and naphthalene oxide.

Naphthalene is a commercially important compound produced from coal tar and petroleum. The toxicology of naphthalene shows unusual species and tissue specificity. The rodent $LD_{50}S$ are 380 mg/kp ip in male Swiss-Webser mice (Shank, R. C., Barrows, L. P. and Buckpitt, A. R., "Comparative Metabolism of Hydrazide and Naphthalene", *Annual Report to Air Force Aerospace Medical Research Laboratory*, Report No. AFARMAL-TR-80-103, Aerospace Medical Division, Air Force System, Wright-Patterson Air Force Base, Ohio (1980)), which is hereby incorporated by reference, 533 and 710 mg/kg po for male and female CD-1 mice, (Shopp, G. M., White, Jr., K. L. Holsapple, M. P., Barnes, D. W., Duke, S. S., Andersen, A. C., Condie, Jr., L. W. Hayes, J. R., and Borzelleca, J. F., "Naphthalene Toxicity in CD-1 Mice: General Toxicity and Immunotoxicology," *Fundam. Appl. Toxicol.*, 4: 406–419 (1984), which is hereby incorporated by reference, as compared to 2200 and 2400 mg/kg po for male and female Sherman rats (Gaines, T. B., "Acute Toxicity of Pesticides", *Toxicol. Appl. Pharmacol.* 14: 515–534 (1969)), which is hereby incorporated be reference). Tissue binding is not necessarily indicative of toxicity or metabolism at that site, with similar binding levels occurring in lung and liver, but toxicity is limited to the Clara cells of the lung. For the lung, increases in binding are associated with increasing severity of tissue damage. Sensitivity of the target cell or circulation of reactive metabolites from the liver to the lung have been proposed as explanations for toxicity (Buckpitt, A. R. and Franklin, R. B., "Relationship of Naphthalene and 2-methylnaphthalene Metabolism to Pulmonary Bronchiolar Epithelial Cell Necrosis", *Pharmac. Ther.* 41: 393–410 (1989)), which is hereby incorporated by reference). A schematic diagram of naphthalene and naphthalene oxide biotransformation are depicted in FIG. 18.

We have developed a physiologically based pharmacokinetic model (PBPK) for naphthalene. Previous PBPKs have been used to explain differences in toxicity for different species and routes of administration and to explore possible mechanisms of toxicity (e.g., Anderson, M. E., Clewell III, M. J., Gargas, M. L., Smith, F. A., and Reitz, R. M., "Physiologically Based Pharmacokinetics and the Risk Assessment Process for Methylene Chloride", *Toxicol. Appl. Pharmacal*, 87: 185–205 (1987), which is hereby incorporated by reference). Sufficient in vitro data for mouse tissue exists to construct such a model for naphthalene. The glutathione (GSH) status of the tissues is important in naphthalene toxicology, and the model for glutathione depletion and resynthesis developed by (D'Souza, R. W., Francis, W. R., and Andersen, M. E., "Physiological Model for Tissue Glutathione Depletion and Increased Resynthesis after Ethylene Dichloride Exposure", *J. Pharmacol. Exp. Ther.* 245: 563–568 (1988), which is hereby incorporated by reference) has been incorporated into this model.

Our model allows the reactive metabolites, the two naphthalene oxide enantiomers, to circulate throughout the body, unlike previous PBPKs where metabolites have been restricted to the tissues in which they are generated. Our model is essentially a system of parallel PBPKs which are bridged by the biotransformation of naphthalene to naphthalene oxide in the lung and liver.

This model is valuable both as a way to compare species and route differences for naphthalene toxicology, and because it can serve as a model for other compounds with circulating metabolites. Circulating metabolites have been offered as explanations for the toxicity of 3-methylindole (Yost, G. S., Kuntz, D. J., and McGill, L. D., "Organ Selective Switching of 3-methylindole Toxicity by Glutathione Depletion", *Toxicol App. Pharmacol.* 103: 40–51 (1990), which is hereby incorporated by reference), dichlorethylene (Okine, L. K. and Gram, T. E., "In vitro Studies on the Metabolism and Covalent Binding of ($^{14}$C)1,1-dichloroethylene by Mouse Liver, Kidney and Lung", *Biochem. Pharmacol.* 35: 2789–2795 (1986), which is hereby incorporated by reference), and bromobenzene (Casini, A. F., Ferrali, M., Pompella, A., Maellaro, E., and Comporti, M., "Lipid Peroxidation and Cellular Damage in Extrahepatic Tissues of Bromobenzene-intoxicated Mice", *Am. J. Pathol.* 123: 520–531 (1986), which is hereby incorporated by reference).

METHODS

Model Structure

The model structure is similar to that of D'Souza, et al., supra, is depicted in FIG. 1, and is described as follows:

Mass Balance Equations for Naphthalene and Napthalene Oxide d CLUN/dt=QC*(CVN-CAN)/WLU-(VLUNRS*CLUN/(CLUN+KMLUNRS) +VLUNSR*CLUN/(CLUN+KMLUNSR))*UNIT1 d CL1N/dt=QLI*(CPVN-CVLIN)/WLI-(VLINRS*CLIN/(CLIN+KMLINRS) +VLINSR*CLIN/(CLIN+KMLINSR))*UNIT2 d CKN/dt=QK*(CAN-CVKN)/WK d CFN/dt=QF*(CAN-CVFN)/WF d CON/dt=QO*(CAN-CVON)/WO d CKRS/dt=QK*(CARS-CVKRS)/WK-KNOH*CKRS d CFRS/dt=QK*(CARS-CVFRS)/WK-KNOH*CFRS d CORS/dt=QK*(CARS-CVORS)/WK-KNOH*CORS

The mass balance equations for 1S, 2R-naphthalene oxide are the same as for 1R, 2S-naphthalene oxide, with "SR" substituted for "RS."

Partitioning

CAN=CLUN/PLUB

CVLIN=CLIN/PLIB

The equations for lung, kidney, fat, and other tissues are the same as for the liver, with LU, K, F AND O replacing L1.

Mixing

CVN=(CVLIN*QLI+CCVKN*QK+CVFN*QF+CVON*QO/QC

For CVRS and CVSR, replace N in the above equation with RS or SR.

CPVN=CAN+KIP/QLI(ip dose)

CPVN=CAN+KUP*AOR*EXP(-KUP*T)/QLI(oral dose)

Accounting for non-enzymatic rearrangement in the blood.

CARS$_2$=CARS$_1$(1+KNOH*WBL*2/3/QC)

CVRS$_2$=CVRS$_1$(1+KNOH*WBL/3/QC)

For CASR and CVSR replace RS with Sr.

GSH mass balance and GSH synthetase synthesis d CLUG/dt=KLUG/WLU-KLUGS*CLUG+CLUSR/(CLUSR+KMNOC))*UNIT5 d KLUG/dt=(KLUGSS+KMGSS)/(CLIGPT+KMGSS)-KGSD*KLUG

For liver, replace LU with L1 and UNIT5 with UNIT6.

Conversion to dihydrodiol, GSH conjugates, and total metabolites

| | | |
|---|---|---|
| d CLUN/dt | = | QC*(CVN − CAN)/WLU − (VLUNRS*CLUN/(CLUN + KMLUNRS) + VLUNSR*CLUN/(CLUN + KMLUNSR))*UNIT1 |
| d CLIN/dt | = | QLI*(CPVN − CVLIN)/WLI − (VLINRS*CLIN/(CLIN + KMLINRS) + VLINSR*CLIN/(CLIN + KMLINSR))*UNIT2 |
| d CKN/dt | = | QK*(CAN − CVKN)/WK |
| d CFN/dt | = | QF*(CAN − CVFN)/WF |
| d CON/dt | = | QO*(CAN − CVON)/WO |
| d CLURS/dt | = | QC*(CVRS − CARS)/WLU + VLUNRS*CLUN/(CLUN + KMLUNRS)*UNIT1 − VLURSD*CLURSD/(CLURSD + KMRSDI)*UNIT1 − VLUNOC*CLUN*CLUG/(CLUN + KMNOC)/(CLUG + KMGSS)*UNIT5 − KNOH*CLURS − (KP*CLURS/WLU)*UNIT3 |
| d CLIRS/dt | = | QLI*(CARS − CVLIRS)/WLI + VLINRS*CLIN/(CLIN + KMLINRS) *UNIT2 − VLIRSD*CLIRSD/(CLIRSD + KMRSDI)*UNIT2 − VLUNOC*CLIN*CLIG/(CLIN + KMNOC)/(CLIG + KMGSS)*UNIT6 − KNOH*CLIRS − (KP*CLIRS/WLI)*UNIT4 |

| | |
|---|---|
| d DIOL/dt | = (VLURSD*CLURSD/(CLURSD + KMRSDI) + VLUSRD*CLUSRD/(CLUSRD + KMSRDI))*UNIT1*WLU + (VLIRSD*CLIRSD/(CLIRSD + KMRSDI) + VLISRD*CLISRD/(CLISRD + KMSRDI))*UNIT2*WLI |
| d CONJUGATE2/dt | = VLUNOC*(CLUG/(CLUG + KMGC)) *(CLURS/(CLURS + KMNOC)*UNIT5*WLU + VLINOC*(CLIG/(CLIG + KMGC))*(CLIRS/(CLIRSIKMNOC* *UNIT6*WLI |

For conjugates 1 and 3, replace RS with SR in the above equation.

| | |
|---|---|
| d N/dt | = (VLUNRS*CLUN/(CLUN + KMLUNRS) + VLUNSR*CLUN*(CLUN + KMLUNSR))*UNIT1 + (VLINRS*CLIN/(CLIN + KMLINRS) + VLINSR*CLIN/(CLIN + KMLINSR))*UNIT2 |

Covalent Binding d (Binding of RS in LU)/dt-KP*CLURS

For liver, replace LU with L1, for SR, replace RS with SR.

Nomenclature for Mass Balance Equations

Decoding Abbreviations

First letter(s): parameter type
C: Concentration
K: Reaction rate
KM: Michaelis constant
P: Partition coefficient
Q: Flow rate
V: Maximum reaction rate
W: Weight
Next letter(s): anatomical location
A: Arterial blood
B, BL: Blood
C: Cardiac
F: Fat
K: Kidney
LI: Liver
LU: Lung
Q: Other tissues
PV: Portal vein
V: Venus blood
If these letters do not appear, the parameter is not tissue specific.
Next group of letters: Compound (s)
C: Naphthalene oxide-glutathione conjugate
D, DI: Naphthalene 1, 2 dihydrodiol
G: Glutathione
GS: Glutatione synthetase
N: Naphthalene
NO: 1R, 2S, 2R-naphthalene oxide
NOH: 1-Naphthol
P: Protein
RS: 1R, 2S-naphthalene oxide
SR: 1S, 2R-naphthalene oxide If two compound abbreviations are part of one parameter name, it involves reaction of the first compound to form the second.

Final letters:
For rates:
D: Degradation
S: Synthesis
For concentrations:
SS: Steady state
PT: A prior time, T-TD
Examples: VLURSD=maximum velocity (v) for reaction in the lung (LU) of 1R, 2S-napthalene oxide (RS) to dihydrodiol (D).
KLIGGS: rate (K) in the liver (LI) of glutathione (G) at steady state (SS).
Other nomenclature:
AOR: Amount of oral dose which is bioavailable
KUP: Rate or oral uptake
T: Time
TD: Time Delay for glutathione synthetase synthesis
UNIT: Unit conversions for scaling up reaction rates from mg protein to whole organ levels
KIP: Rate of ip uptake A Fortran computer program was written to run on a VAX station using VMS 5.4. The differential equations are integrated numerically using LSODA (Livermore Solver for Ordinary Differential Equations, with Automatic Switching Method for Stiff and Non-stiff Problems, Linda R. Petzold and Alan C. Hindmarch, Lawrence Livermore National Laboratory, Livermore, Calif.).

Determination of Anatomical Parameters

A model based on a 22-g mouse was developed. The blood volume was calculated from the allometric relation in Kaplan, H. M., Brewer, N. R. and Blair, W. H., *Physiology*, Chapter 11, "In The Mouse in Biomedical Research", Vol. III, pp. 247–292 (1983), which is hereby incorporated by reference) and divided between venous and arterial blood 2:1 as in Gearhart, J. M., Jepson, G. W., Clewell III, H. J., Andersen, M. E., and Conolly, R. B., "Physiologically Based Pharmacokinetic Model for the Inhibition of Acetylcholinesterase by Diisopropylfluorophosphate", *Toxicol. Appl. Pharmacol.* 106, 295–310 (1990), which is hereby incorporated by reference. The weight of the lung, liver, kidney and fat were also calculated from allometric relations disclosed in Calder III, W. A., "Size, Function and Life History"

(1984), and Andersen, M. E., Clewell III, H. J. Gargas, M. L., Smith, F. A., and Reitz, R. H., "Physiologically Based Pharmacokinetics and the Risk Assessment Process for Methylene Chloride," *Toxicol. Appl. Pharmacol.* 87: 185–205 (1987), which is hereby incorporated by reference, calculated the volume of rapidly and slowly perfused tissues as totaling 83 percent of the body weight. The "other tissues" in our model are assumed to weigh 83 percent of the body weight less the weight of the blood and kidney.

The cardiac output was calculated as in Kaplan, et al., supra, and the renal blood flow as in Calder, supra. The liver and fat are assumed to receive 24 and 5 percent of the cardiac output (Andersen et al., supra). The remainder of the cardiac output flows to the other perfused tissues.

Anatomical parameters for a 220-g rat are the same as those used in Gearhart, J. M., Jepson, G. W., Clewell III, M. J., Anderson, M. E., and Conolly, R. B., "Physiologically Based Pharmacokinetic Model for the Inhibition of Acetylcholinesterase by Diisopropylfluorophosphate", *Toxicol. Appl. Pharmacol.* 106: 293–310 (1990), which is hereby incorporated by reference, with the volumes and flows for rapidly and slowly perfused tissues, brain, and diaphragm summed for our lumped "other tissues" compartment.

The parameters used in simulation are summarized in Table 1.

TABLE 1

Anatomical Parameters Used In Naphthalene PBPK

|  | Mouse | Rat |
|---|---|---|
| Weights in g |  |  |
| Body | 22.00 | 220.00 |
| Blood | 1.54 | 13.20 |
| Lung | 0.25 | 2.53 |
| Liver | 1.19 | 8.80 |
| Kidney | 0.27 | 1.61 |
| Fat | 0.80 | 15.40 |
| Other perfused tissues | 16.45 | 171.95 |
| Blood flow rates in mL/min |  |  |
| Cardiac output | 8.39 | 76.20 |
| Liver | 2.01 | 19.05 |
| Kidney | 2.76 | 15.24 |
| Fat | 0.42 | 6.86 |
| Other perfused tissues | 3.20 | 35.05 |

Determination of the Tissue:Blood Partition Coefficients

From the known solubility characteristics of naphthalene in air, water (Vargartik, N. B., *Handbook of Physical properties of Liquids and Gases* (2d ed. 1975), which is hereby incorporated by reference, and octanol-water (Hansch, C. and Leo, A., *Substituent Constants for Correlation Analysis in Chemistry and Biology* (1979), which is hereby incorporated by reference, systems, it is possible to predict tissue:blood partition coefficients (Abraham, M. H., Kamlet, M. J., Taft, R. W., Doherty, R. M., and Weathersby, P. K., "Solubility Properties in Polymers and Biological Media. 2. The Correlation and Prediction of the Solubilities of Non-electrolytes in Biological Tissues and Fluids", *J. Med. Chem.* 28: 865–870 (1985), which is hereby incorporated by reference). Tissue:blood partition coefficients were calculated for lung (0.627), liver (5.41), kidney (3.87) fat (796), and muscle (4.13). The partition coefficient for muscle was used for the other tissues compartment of our model. The same partition coefficients were used for naphthalene and naphthalene oxide.

The partition coefficient for lung was found to be inconsistent with levels of covalent binding occurring in this tissue. For simulations, a value of 4.0 was used instead. This value is more in line with the partition coefficients for the other non-adipose tissues. In PBPKs, the same partition coefficient is usually used for all well-perfused tissues, including the lung (e.g. D'Souza, supra, Andersen et al. (1985), supra, and Ward, R. C., Travis, C. C., Hetrick, D. M., Anderson, M. E., and Gargas, M. L., "Pharmacokinetics of Tetrachloroethylene", *Toxicol. Appl. Pharmacol.* 93: 108–117 (1988), which is hereby incorporated by reference.

Determination of GSH Resynthesis Parameters

Steady state values of 2.2 and 6.6 mM were used for lung and liver GSH concentrations in the mouse. The lung value is an average of two literature values (O'Brien, K. A. F., Smith, L. L., and Cohen, G. M., "Differences in Naphthalene-induced Toxicity in the Mouse and Rat", *Chem. Biol. Interact.* 55: 109–122 (1985), which is hereby incorporated by reference), and Warren, D. L. Brown, Jr., D. L., and Buckpitt, A. R., "Evidence for Cytochrome P-450 Mediated Metabolism in the Bronchiolar Damage by Naphthalene", *Chem. Biol. Interact.* 40: 287–303 (1982), which is hereby incorporated by reference). The liver value is an average of several appearing in the literature ranging from 4.1 mM (Buonarati, M., Morin, D., Plopper, C. and Buckpitt, A., "Glutathione Depletion and Cytotoxicity by Naphthalene 1,2-oxide in Isolated Hepatocytes", *Chem. Biol. Interact.* 71: 147–165 (1989) and 8.6 mM (Richieri, P. R. and Buckpitt, A. R., "Gluthathione Depletion by Naphthalene in Isolated Hepatocytes and by Naphthalene Oxide in vivo", *Biochem. Pharmacol.* 37: 2473–2478 (1988), which is hereby incorporated by reference).

Initially, the parameter values for the model were calculated as in D'Souza, supra, but the different body and organ weights and desired steady state levels lead to discrepancies. The values for synthesis of GSH synthetase (KLUGSS and KLIGSS in the model) (see nomenclature in Example 2) were adjusted to yield the desired steady state GSH concentrations. This adjustment was subsequently demonstrated to be satisfactory for the liver but not the lung. Adjusting the rate of GSH degradation in the lung (KLUGD) produced better results. For the rat, calculating the GSH resynthesis parameters as in D'Souza, supra, gave acceptable steady state GSH levels. The kinetic constants used in the GSH model are summarized in Table 2.

TABLE 2

|  | Mouse | Rat |
|---|---|---|
| Degradation rates in 1/min |  |  |
| GSH synthetase | 0.005 | 0.0025 |
| GSH in lung | 0.00209 | 0.00304 |
| GSH in liver | 0.006 | 0.00304 |
| Synthesis rates of GSH synthetase in nmole/min/min |  |  |
| in lung | 0.00575 | 0.0212 |
| in liver | 0.236 | 0.366 |
| Steady state GSH levels in μM |  |  |
| in lung | 2200 | 1100 |
| in liver | 6600 | 5470 |
| Km for GSH synthetase synthesis in μM | 2000 | 2000 |
| Time delay in GSH synthetase synthesis in min | 60 | 60 |

Determination of Kinetic Parameters for Naphthalene Biotransformation: Phase I Reactions in the Mouse Biotransformation rates of naphthalene at initial concentrations of 0.05, 0.1 and 1.0 mM by lung and liver microsomes have been determined (O'Brien, et al. (1985), supra, Buckpitt, A. R., Bahnson, L. S., and Franklin, R. B., "Hepatic and Pulmonary Microsomal Metabolism of Naphthalene to Glutathione Adducts: Factors Affecting the Relative Rates of Conjugate Formation", *J. Pharmacol. Exp. Ther.* 231: 291–300 (1984), which is hereby incorporated by reference), and Buckpitt, A. R., Castagnoli, Jr., N., Nelson, et al., "Stereoselectivity of Naphthalene Epoxidation by Mouse, Rat, and Hamster Pulmonary, Hepatic and Renal Microsomal Enzymes", *Drug Metab. Dispos.* 15: 491–498 (1987), which is hereby incorporated by reference). Assuming Michaelis-Menten kinetics, fitting s/v vs s was used to provide Vmax and Km values. Since mouse liver produces the 1R,2S- and 1S,2R-naphthalene oxide enantiomers in equal amounts at all substrate concentrations (Buckpitt, et al., 1987, supra), the calculated Vmax was divided by two to give the production rates for each enantiomer.

For the lung, the biotransformation of naphthalene was modeled as the sum of two separate reactions, each producing a different enantiomer, with the Vmax's summing to the value calculated as described above. The 1R,2S-naphthalene oxide/1S,2R-naphthalene oxide ratio (RS/SR) is 30:1 and 10:1 for naphthalene concentrations of 0.015 and 1.0 mM (Buckpitt and Franklin, 1989, supra, and Buckpitt, et al., 1987, supra). vmax's and Km's were fit to the reaction rate and ratio data by trial and error.

Determination of Kinetic Parameters for Naphthalene Biotransformation: Phase II Reactions in the Mouse The Km values used for conversion of 1R,2S- and 1S,2R-naphthalene oxide to 1,2 dihydrodiol by epoxide hydrolase (EH) were those determined for rat liver microsomes (van Bladeren, P. J., Sayer, J. M., Ryan, D. E., Thomas, P. E., Levin, W., and Jerina, D. M., "Differential Stereoselectivity of Cytochrome P-450b and P-450c in the Formation of Naphthalene and Anthracene 1,2-oxides", *J Biol Chem* 260: 10226–10235 (1985), which is hereby incorporated by reference). Vmax's for conversion of each enantiomer in the lung and liver were determined by trial and error fit to data for incubations of naphthalene and microsomes, with no GSH present (O'Brien et al., 1985, supra). For determining the EH Vmax's, the experimental naphthalene concentration profiles were used rather than the values predicted by fitting a number of experiments (as described in the previous section).

The rate of reaction of naphthalene oxide with GSH is assumed to be of the form V=Vmax*{1GSH/(GSH+ Kml)}*{NO/(NO+Km2)}. Nonenzymatic formation of naphthalene oxide-GSH conjugates is slow or non-existent (Garle, M. J. Fry, J. R., "Detection of Reactive Metabolites in vitro", *Toxicology* 54: 101–110 (1989), which is hereby incorporated by reference). Work with partially purified sheep liver glutathione-S-arene oxide transferase has provided Km's for conjugation of GSH and racemic naphthalene oxide at pH 7.4 (Hayakawa, T., LeMahieu, R. A., and Udenfriend, S., "Studies on Glutathione-S-arene Oxide Transferase—a Sensitive Assay", *Arch. Biochem. Biophys.* 162: 223–230 (1974), which is hereby incorporated by reference). Individual glutathione-S-transferase isozymes are enantioselective with respect to naphthalene oxide (O'Brien, K. A. F., Suverkropp, C., Kanekal, S., Plopper, C. G., and Buckpitt, A. R., "Tolerance to Multiple Doses of the Pulmonary Toxicant, Naphthalene", *Toxicol. Appl. Pharmacol.* 99: 487–500 (1989), which is hereby incorporated by reference), but GSH conjugation proceeds equally fast with 1R, 2S- and 1S, 2R-naphthalene oxide (Buonarati, M., Jones, A. D., and Buckpitt, A., "In vivo Metabolism of Isomeric Naphthalene Oxide Glutathione Conjugates", *Drug Metab. Dispos.* 18: 183–189 (1990), which is hereby incorporated by reference). Therefore Vmax's for conjugation with each enantiomer are assumed equal, and the Km for reaction with each enantiomer is assumed to be one-half of the value reported for racemic naphthalene oxide.

The naphthalene oxide-GSH conjugation Vmax's were determined by fitting data from incubations of lung and liver microsomes and cytosolic protein with GSH or hepatocyte cultures with concentrations of naphthalene ranging from 0.005 to 1.5 mM (Buckpitt et al., 1984, supra, and Richieri, P. R. and Buckpitt, A. R., "Efflux of Naphthalene Oxide and Reactive Naphthalene Metabolites from Isolated Hepatocytes", *J. Pharmacol. Exp. Ther.* 242: 485–492 (1987), which is hereby incorporated by reference).

Determination of Kinetic Parameters for Naphthalene Biotransformation in the Rat Determination of Vmax's and Km's for naphthalene oxide production and Vmax's for GSH conjugates and dihydrodiol production in rat microsomes were done in the same way as for the mouse. Sources of data were Buckpitt, et al, 1987, supra, Hesse, S. and Mezger, M., "Involvement of Phenolic Metabolites in the Irreversible Protein-binding of Aromatic Hydrocarbons: Reactive Metabolites of [$^{14}$C]-naphthalene and [$^{14}$C] 1-naphthol Formed by Rat Liver Microsomas", *Mol. Pharmacol.* 16: 667–675 (1979) which is hereby incorporated by reference, O'Brien et al., 1985, supra, van Bladeren et al., 1985, supra, and Yost, G. S., Buckpitt, A. R., Roth, R. A., and McLemore, T. L., "Mechanisms of Lung Injury by Systematically Administered Chemicals", *Toxicol. Appl. Pharmacol.* 101: 179–195 (1989), which is hereby incorporated by reference.

Non-enzymatic Reactions of Naphthalene Oxide

The first order rate constant for non-enzymatic rearrangement of naphthalene oxide to 1-naphthol has been reported (van Bladeran et al., 1985, supra). The rate of covalent binding was determined from data reported for incubations of hepatocytes with naphthalene oxide (Buonarati et al., 1989, supra).

Scaling Reactions to Whole-organ Rates

To scale reaction rates based on microsomal and cytosolic protein, conversion factors are used. The same values were used for mouse and rat. Levels of 3.67 and 16.4 mg microsomal protein/g of tissue have been reported for rat lung and mouse liver (Rietjens, I. M. C. M., Dormans, J. A. M. A., Rombout, P. J. A., and Van Brae, L., "Qualitative and Quantitative Changes in Cytochrome P-450-dependent Xenobiotic Metabolism in Pulmonary Microsomes and Isolated Clara cell Populations Derived from Ozone Exposed Rats", *J. Toxicol. Environ. Health* 24: 515–531 (1988), which is hereby incorporated by reference, and Garle and Fry, 1984, supra). The levels of cytosolic protein are 30.5 and 74 mg/g in these tissues (Rietjens et al., 1988, supra, and Disimplico, P., Jensson, H. and Mannervik, B., "Effects of Inducers of Drug Metabolism on Basic Hepatic Forms of Mouse Glutathione Transferase", *Biochem. J.* 263: 679–685 (1989), which is hereby incorporated by reference), but Buckpitt et al., 1984, supra, showed that increasing the cytosolic/microsomal protein ratio above 0.5 does not affect the product distribution in the lung, and increasing the ratio above 1.1 has no effect in the liver. Thus reaction rates on the basis of cytosolic protein are scaled as if there were 1.8 and 16.4 mg/g of cytosolic protein in the lung and liver.

The amounts of total protein are 13.8 mg/mouse lung (Kanekal, et al., 1990, supra), and 112 mg/mouse liver (Cha, Y. N. and Bueding, E., "Effect of 2(3) Tert-butyl-4-hydroxyanisole Administration on the Activities of Several Hepatic Microsomal and Cytosoplasmic Enzymes in Mice", *Biochem. Pharmacol.* 28: 1917–1921 (1979), which is hereby incorporated by reference). For the rat, these values are multiplied by the ratio of the organ weights in rat and mouse.

Oral Uptake Rates

Uptake from an oral dose was modeled as first order with respect to the amount yet to be absorbed. D'Souza and Andersen, 1988, supra report that oral absorption rates of 1.0 hr are typical for halogenated hydrocarbons administered po in a corn oil vehicle, and used 0.5–1.0/hr (0.008–0.017/min) for vinylidene chloride. An initial estimate in this range was used for naphthalene.

Bioavailability

After oral administration of 2 mg naphthalene to a rat, 87–91 percent of the dose was recovered as metabolites within 72 hrs (Bakke, J., Struble, C., Gustafsson, J. A., and Gustaffson, B., "Catabolism of Premercapturic Acid Pathway Metabolites of Naphthalene to Naphthalene to Naphthols and Methylthio-containing Metabolites in Rats", *Proc. Natl. Acad. Sci. USA* 82: 668–671 (1985), which is hereby incorporated by reference). Eighty-one percent of a 45 mg/kg dose of 1 naphthol was recovered in 72 hours. Other aromatics have demonstrated bioavailabilities of 57–70 percent (Brouwer, K. R. and McNamara, P. J., "Influence of Pregnancy on the Pharmacokinetic Disposition of Two Aromatic Retinoids (Etrinate and Acitretin) in the Rat. II Single and Multiple Oral Dosing Studies", Drug Metab. Dispos. 17: 625–655 (1989), which is hereby incorporated by reference, and Bakke, J. E., Davison, K. L., and Larsen, G. L., "Evidence for the Absence of Cysteine S-conjugate N-acetyl Transferase Activity in the Metabolism of Propachlor, Naphthalene, and Dichlobanil in Calves", *Xenobiotica* 20: 801–807 (1990), which is hereby incorporated by reference). Oral bioavailability of 70 and 81 percent were used in simulation.

Simulation of Whole Animal Toxicology

In addition to those equations needed to describe tissue concentrations of naphthalene, the naphthalene oxides and GSH, amounts of naphthalene converted to dihydrodiol and GSH-conjugates or covalently bound were also calculated. See the mass balance equations of Example 2.

In mice pretreated with buthionine sulfoximine (BSO), hepatic and pulmonary GSH are depleted. The proposed mechanism is that BSO blocks GSH synthesis (Griffith, O. W. and Meister, A., "Glutathione: Interorgan Translocation, Turnover and Metabolism", *Proc. Natl. Acad. Sci. USA* 76: 5606–5610 (1979), which is hereby incorporated by reference). Thus, to model the effect of BSO pretreatment, the GSH synthesis rate is set equal to zero, and the initial levels of GSH set to the experimentally measured values. The natural turnover of GSH by degradation is allowed to continue, in addition to depletion by conjugation with naphthalene oxide.

Forty-eight hours after administration of xylene, GSH levels and metabolism of naphthalene by liver microsomes return to normal, but metabolism by lung microsomes proceeds at 56 percent of the normal rate (Buckpitt, A. R. and Warren, D. L., "Evidence for the Formation, Export, and Covalent Binding of Reactive Metabolites in Extrahepatic Tissues in vivo", *J. Pharmacol. Exp. Ther.* 225: 8–16 (1983), which is hereby incorporated by reference). To model the effect of pretreatment with xylene, VLUNRS and VLUNSR were multiplied by 0.56.

Sensitivity of Mouse PBPK

Three test cases were simulated and compared to the base model to test sensitivity of the model to various parameters. These cases involved disposition of a 100 mg/kg ip dose of naphthalene and the levels of covalent binding in lung and liver resulting from 200 and 400 mg/kg ip doses of naphthalene. The parameters tested for sensitivity included steady state levels of GSH, cardiac output, blood flow to the fat, tissue volumes, and partition coefficients.

RESULTS

Kinetic Parameters for GSH Synthesis

Figure 19:
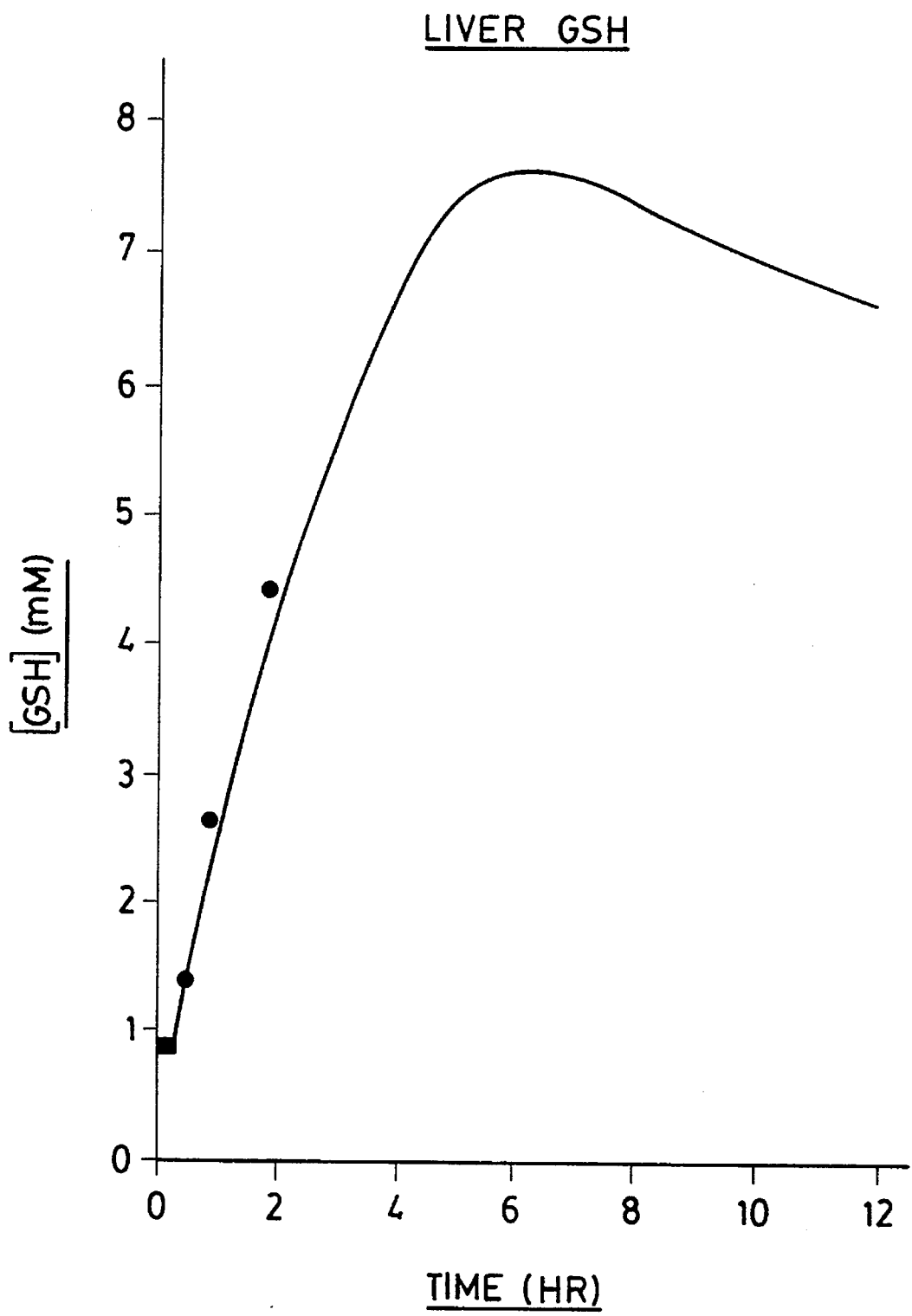
FIG. 19 is a graphical diagram of GSH resynthesis in mouse hepatocytes after 60 μM, 1R,2S-naphthalene oxide is added to a suspension of 1 million hepatocytes/ml.
Figure 20:
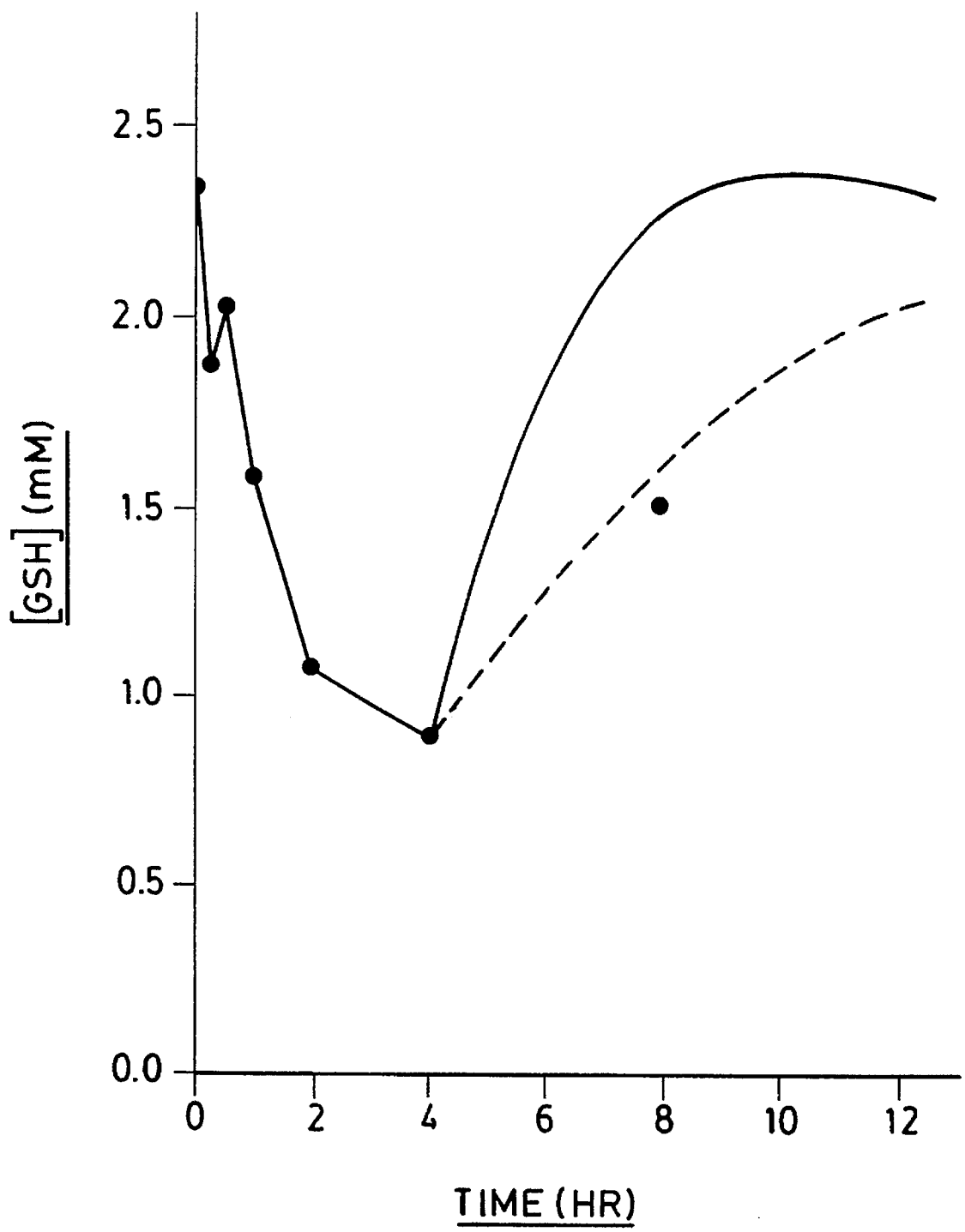
FIG. 20 is a graphical diagram of GSH resynthesis in mouse lung following ip administration of 200 mg/kg naphthalene.
—Simulation 1, KLUGSS=0.163 nmole/min/min, KLUGD=0.006/min—Simulation 2, KLUGSS=0.00575 nmole/min/min, KLUGD=0.0209/min.

The time courses of glutathione recovery in hepatocytes and the lung are shown in FIG. 19 and FIG. 20.

Kinetic Parameters for Naphthalene Biotransformation in the Mouse and Rat

Biotransformation parameters are summarized in Table 3. Comparisons between measured in vitro data and model predictions are found in Tables 4–6.

TABLE 3

| | Biotransformation Parameters | | | |
| --- | --- | --- | --- | --- |
| | Mouse | | Rat | |
| | Vmax nmole/mg/min | Km μM | Vmax mole/mg/min | Kmn μM |
| Phase I Reactions | | | | |
| Lung | | | | |
| N to 1R, 2S NO | 9.0 | 100 | 1.5 | 400 |

TABLE 3-continued

| | Biotransformation Parameters | | | |
|---|---|---|---|---|
| | Mouse | | Rat | |
| | Vmax nmole/mg/min | Km μM | Vmax mole/mg/min | Kmn μM |
| N to 1S, 2R NO Liver | 1.1 | 400 | 3.4 | 1540 |
| N to 1R, 2S NO | 6.95 | 307 | 1.82 | 400 |
| N to 1S, 2R NO | 6.95 | 307 | 7.28 | 800 |
| Phase II Reactions | | | | |
| Conversion to dihydrodiol | | | | |
| Lung | | | | |
| 1R, 2S NO to diol | 0.7 | | 7.0 | |
| 1S, 2R NO to diol | 7.0 | | 11.45 | |
| Liver | | | | |
| 1R, 2S NO to diol | 2.0 | | 3.0 | |
| 1S, 2R NO to diol | 8.0 | | 4.91 | |
| Km for 1R, 2S NO to dihydrodiol | | 1.0 | | 1.0 |
| Km for 1S, 2R NO to dihydrodiol | | 12.0 | | 12.0 |
| Conjugation with GSH | | | | |
| Lung | 22.5 | | 400 | |
| Liver | 150 | | 500 | |
| Km for 1R, 2S— or 1S, 2R— NO | | 50 | | 50 |
| Km for GSH | | 3300 | | 3300 |

Non-enzymatic reactions:

First order rate constant for rearrangement to 1-napthol: 0.25/min

Binding to protein: 0.2 pmole/mg/min/μM NO

TABLE 4

| Biotransformation of Napthalene by Mouse Lung Microsomes | | | | |
|---|---|---|---|---|
| [N] | predicted | | observed | |
| mM | v | ratio | v | ratio |
| 0.015 | 1.21 | 29 | — | 30[a] |
| 0.05 | 3.12 | 24.5 | 1.33[b] | — |
| 0.10 | 4.72 | 20.5 | 6.01[c] | — |
| 1.0 | 8.96 | 10.4 | 8.3[d] | 10[d] | v: nanomoles of product/mg microsomal protein/minute
ratio: ratio of conjugates of 1R, 2S— and 1S, 2R— napthalene oxide
[a]Data of Buckpitt and Franklin, 1989, supra
[b]Data of O'Brien et al., 1985, supra
[c]Data of Buckpitt et al., 1984, supra
[d]Data of Buckpitt et al., 1987, supra

TABLE 5

| House Microsomes, Incubated With 0.1 mM Naphthalene, After 6 Minutes. | | | | |
|---|---|---|---|---|
| | 1R, 2S NO | 1S, 2R NO | NOH | Diol | Covalently bound |
| Liver: | | | | | |
| Simulation | 2.0 | 2.0 | 5.4 | 13.8 | ND |
| [c]Experiment | ND | ND | 3.5 | 11.9 | 5.8 |
| Lung: | | | | | |
| Simulation | 13.9 | 0.26 | 14.7 | 4.5 | ND |
| [c]Experiment | ND | ND | 21.2 | 4.2 | 7.4 |

TABLE 5-continued

| House Microsomes, Incubated With 0.1 mM Naphthalene, After 6 Minutes. | | | | |
|---|---|---|---|---|
| | 1R, 2S NO | 1S, 2R NO | NOH | Diol | Covalently bound |
| concentrations in nmole/mg | | | | | |

[c]Data of Buckpitt et al., 1984, supra

TABLE 6

| Mouse Liver Microsomes Incubated With 1 mM Naphthalene and 5 mM GSH | | |
|---|---|---|
| | Simulation | Observed[a] |
| 1-naphthol | 1.0 | ND |
| 1,2 dihydrodiol | 2.48 | 2.43 |
| Conjugates 1 and 3 | 3.61 | 3.56 |
| Conjugate 2 | 3.61 | 3.64 |
| Total | 10.6 | ND |
| Expected total | 10.7 | |
| Percent GSH conjugates | 67.5 percent | |
| Rates in nmole/mg/min | | |

[a]Data of Buckpitt et al., 1984, supra

Oral Uptake

Table 7 presents observed levels of mercapturates with predicted amounts of glutathione conjugates. An initial GSH concentration of 6.8 mM was used for rat liver to match the values measured experimentally. Six and one-half hours after administration of a 200 mg/kg oral dose, the liver GSH was 17 percent of the initial concentration (Summer, K. M., Rozman, K., Coulston, F., and Greim, H., "Urinary Excretion of Mecapturic Acids in Chimpanzees and Rats", *Toxical*

*Appl. Pharmacol,* 50: 207–212 (1979), which is hereby incorporated by reference. When 1, 2, and 4 hours are used as times for absorbing half the naphthalene, simulation predicts GSH levels 70, 36, and 30 percent of the initial level 6½ hours after administration of naphthalene.

TABLE 7

GSH Conjugations Subsequent to po Administration of Naphthalene in Corn Oil Vehicle to Rats.

| Dose in mg/kg | Percent recovered as mercapturates[a] | Percent GSH conjugates time for absorption of ½ dose | | |
|---|---|---|---|---|
| | | 1 hr | 2 hr | 4 hr |
| 200 | 26 | 55.8 | 58.3 | 60.2 |
| 75 | 32 | 61.5 | 59.7 | 58.7 |
| 30 | 39 | 58.9 | 58.0 | 57.4 |

[a]Data of Summer et al., supra, 1979.

Simulation of Whole Animal Toxicology

Following administration of 100 mg/kg naphthalene to a mouse by intraperitoneal injection, 39 percent of the dose was recovered as mercapturic acids (Stillwell, W. G., Horning, M. G., Griffin, G. W., and Tsang, W. S., "Identification of New Sulfur-containing Metabolites of Naphthalene in Mouse Urine", *Drug Metab. Dispos.* 10: 624–631 (1982), which is hereby incorporated by reference). By dosing directly with naphthalene oxide-GSH conjugates, ranges for recoveries of each of these conjugates as mercapturic acids have been determined for mice (Buonorati et al., 1990, supra). Assuming conjugates 1, 2, and 3 are produced in a 1:2:1 ratio, the high, average, and low recoveries as mercapturates yield estimates of 61.7, 57.3 and 53.8 percent GSH conjugates resulting from a 100 mg/kg dose. Simulation predicts 64 percent.

Figure 21:
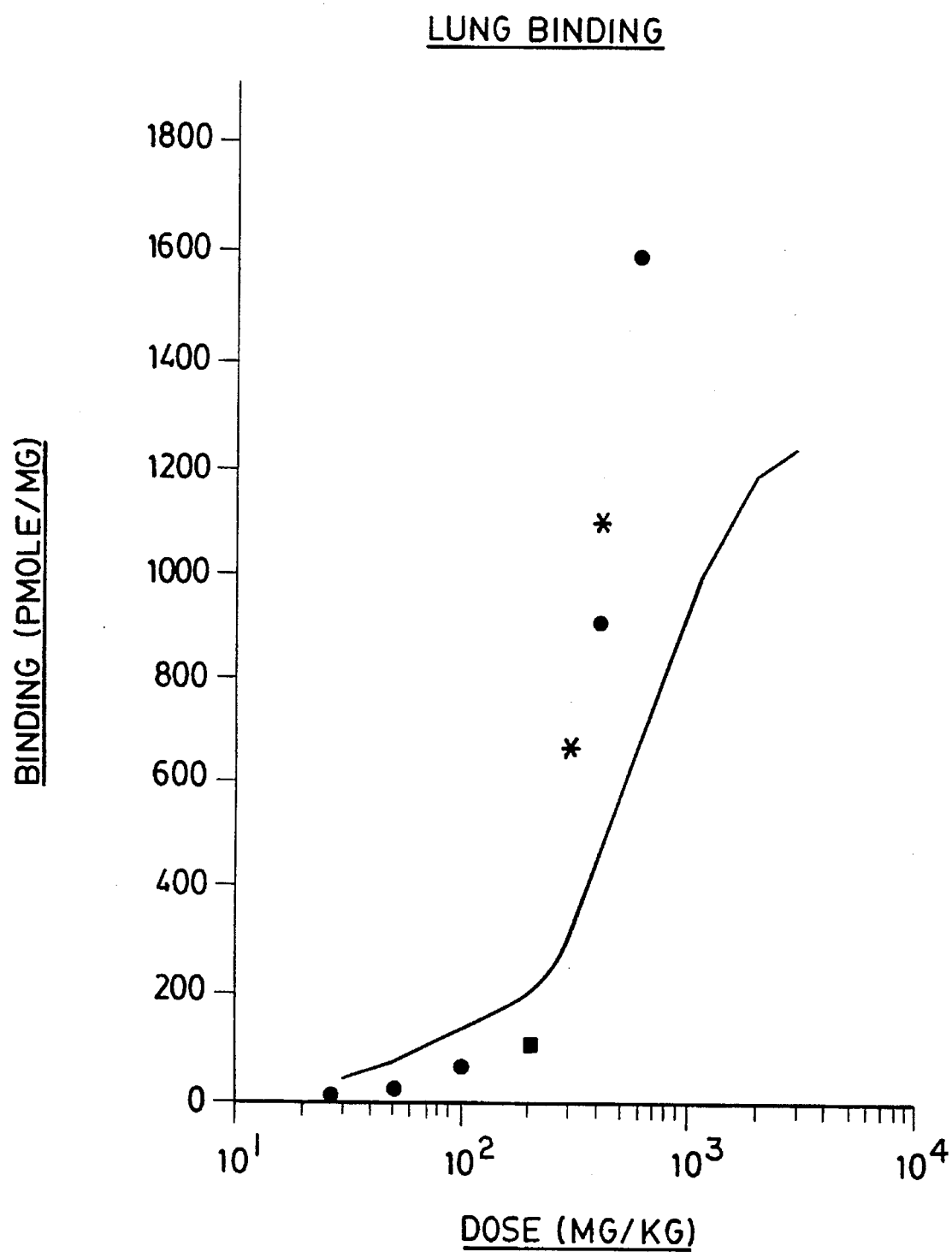
FIG. 21 is a graphical diagram of covalent binding in mouse lung four hours after ip dosing with naphthalene.
Figure 22:
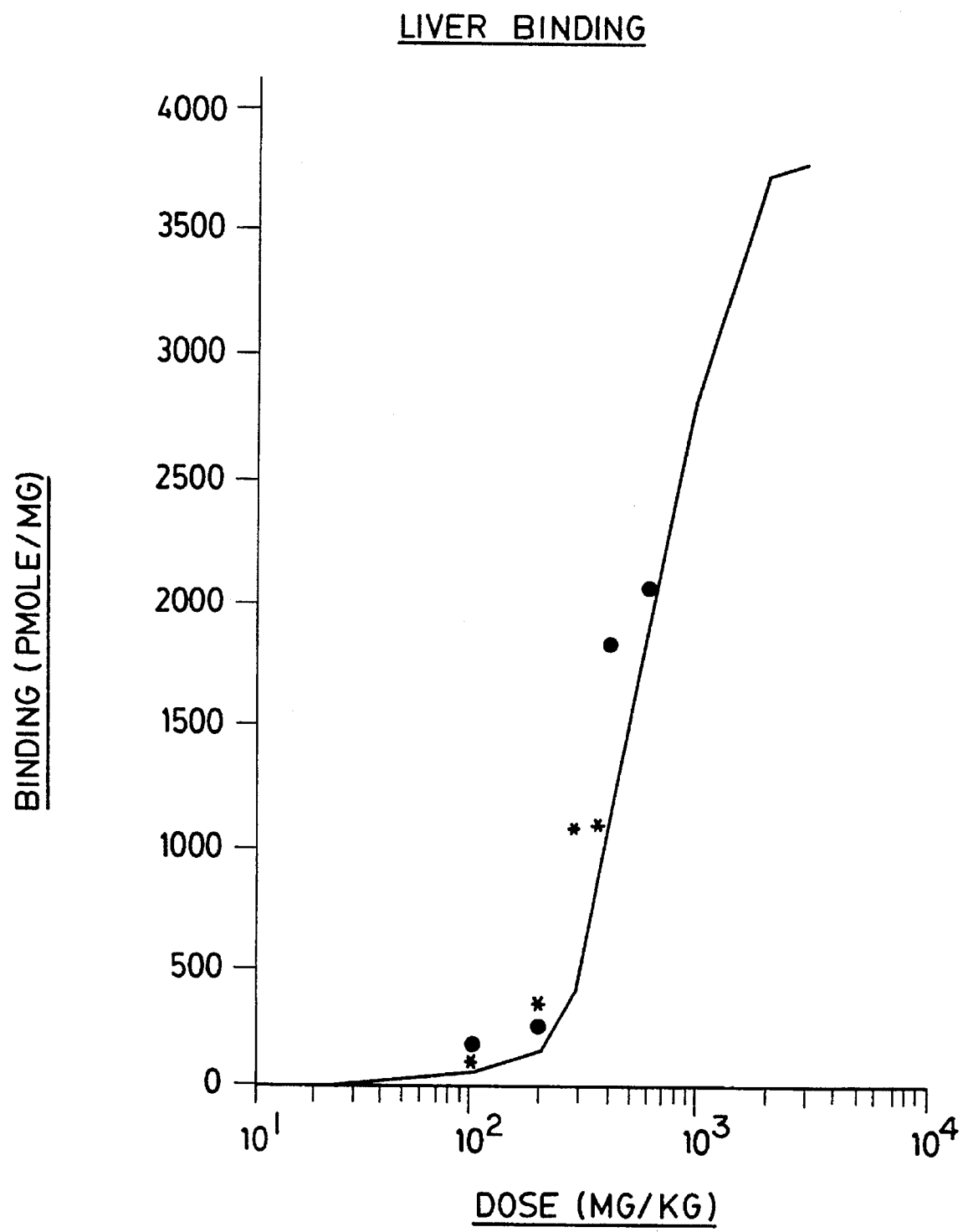
FIG. 22 is a graphical drawing of covalent binding in mouse liver four hours after ip dosing with naphthalene.
Figure 23:
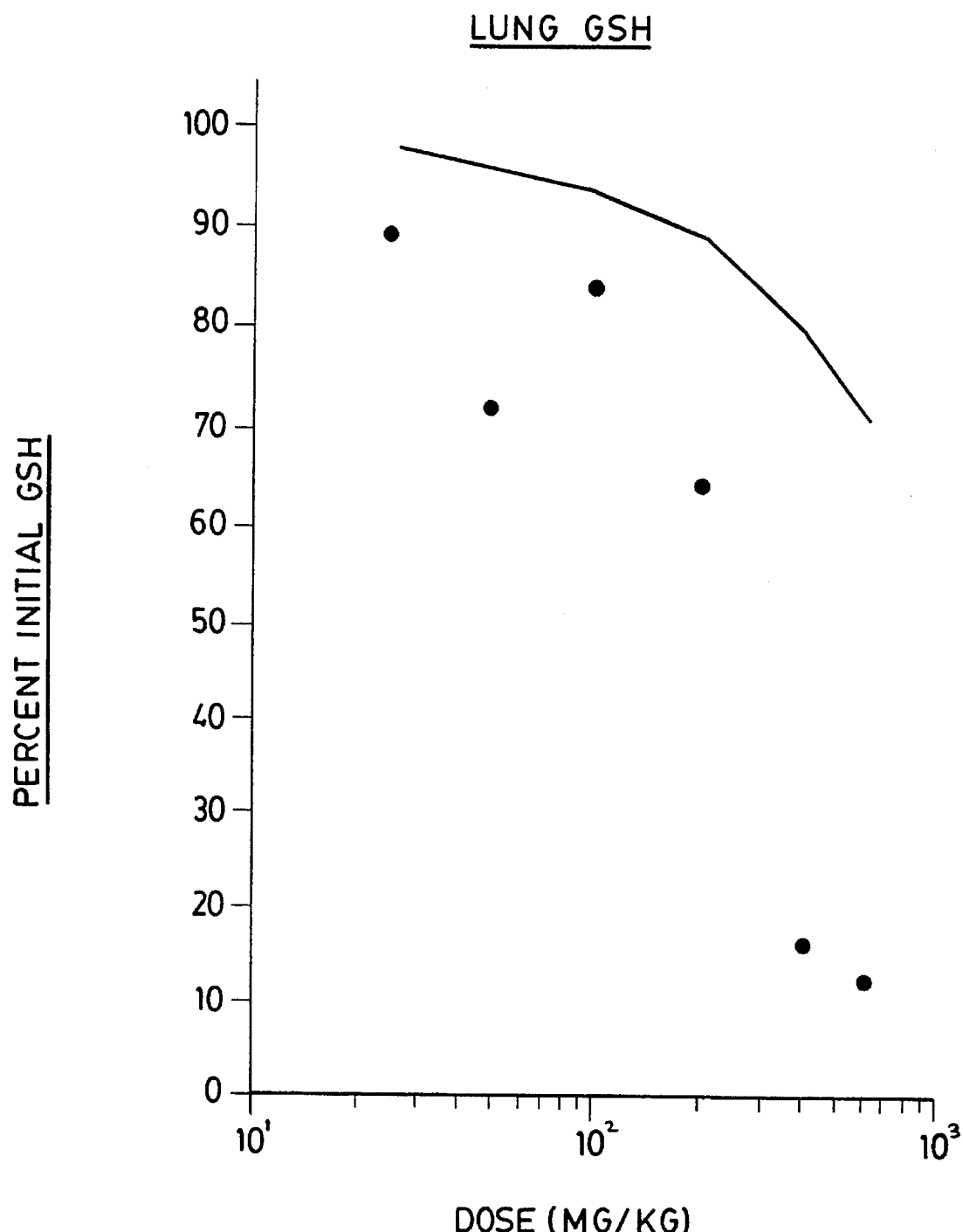
FIG. 23 is a graphical drawing of GSH levels in mouse lung four hours after ip dosing with naphthalene.
Figure 24:
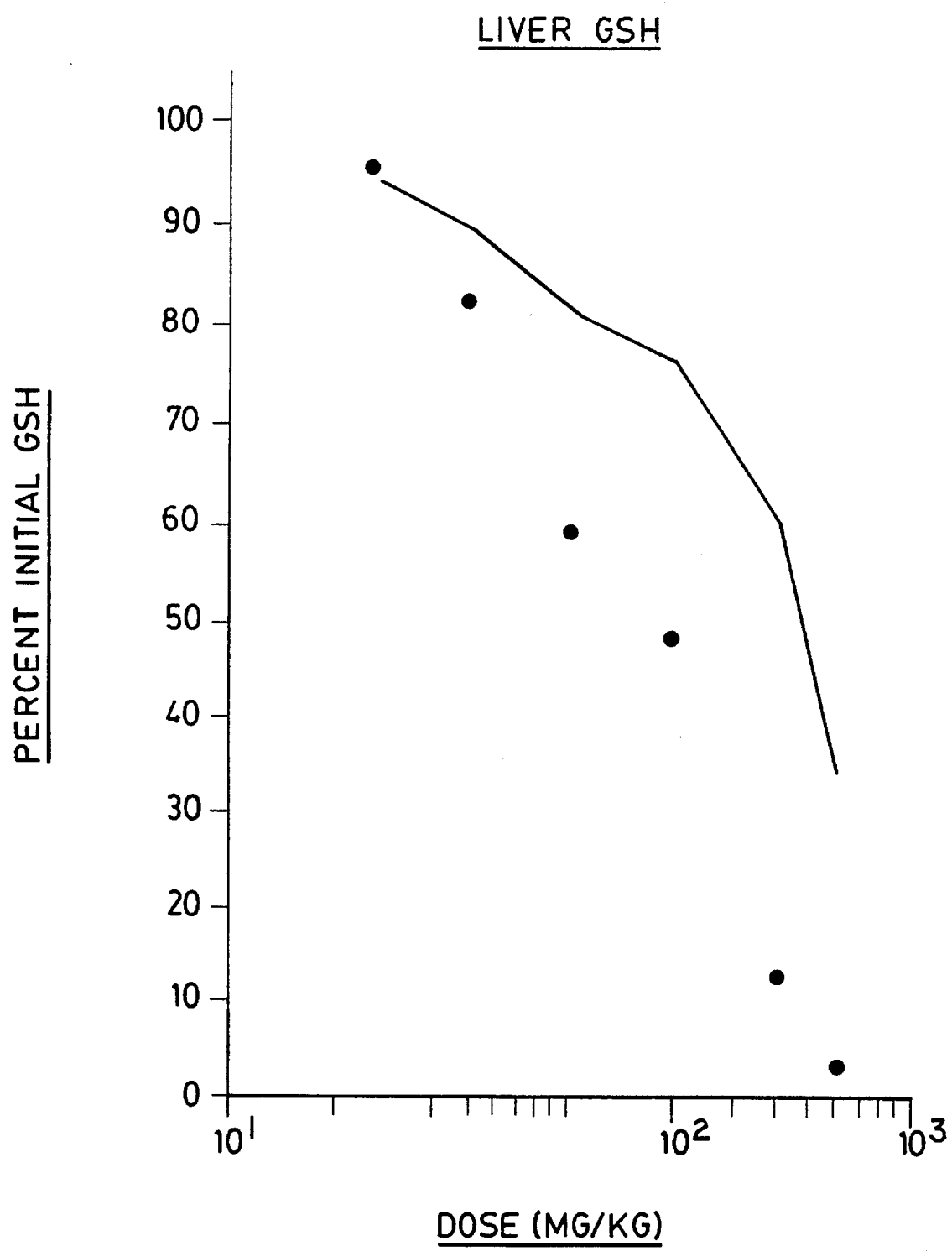
FIG. 24 is a graphical drawing of GSH levels in mouse liver four hours/after ip dosing with naphthalene.

Simulated and experimental values for covalent binding following ip dosing of a mouse are shown in FIGS. 21 and 22. GSH values for these simulations and experiments are shown in FIGS. 23 and 24.

Figure 25:
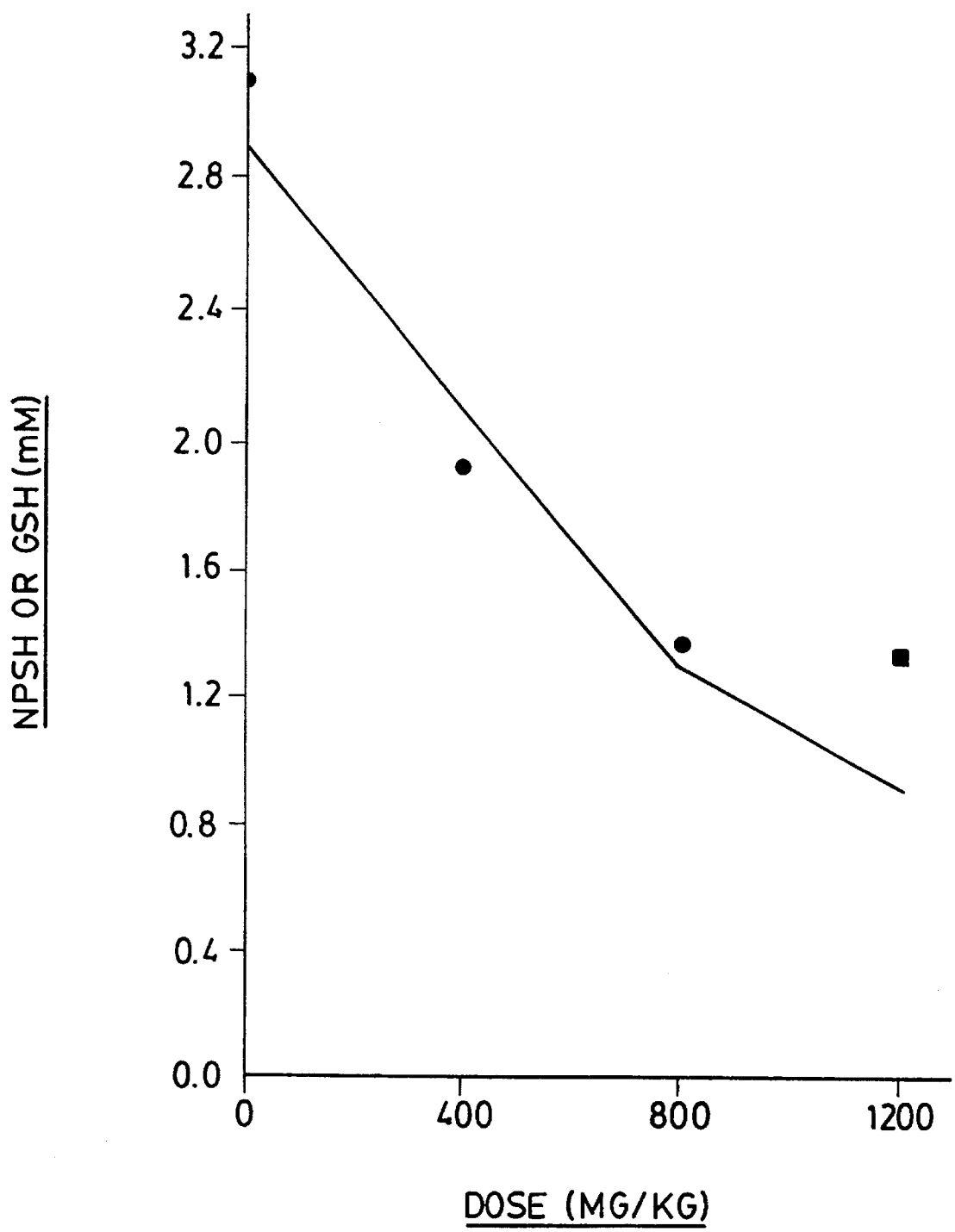
FIG. 25 is a graphical drawing of measured NPSH levels and simulated GSH levels in the lung four hours after ip injection of naphthalene into a rat.
Figure 26:
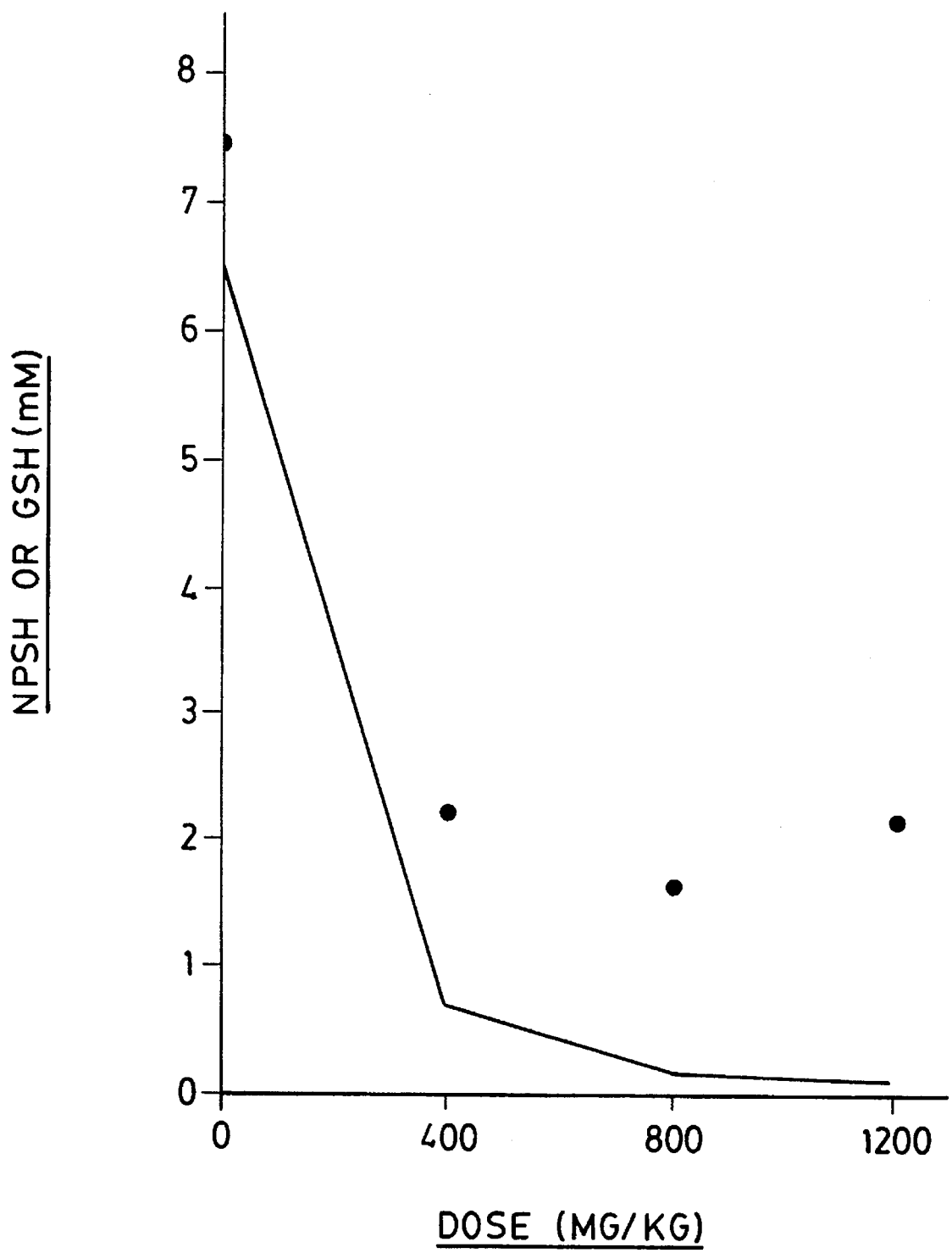
FIG. 26 is a graphical drawing of measured NPSH levels and simulated GSH levels in the liver four hours after ip injection of naphthalene into a rat.

FIGS. 25 and 26 show experimentally determined depletion of nonprotein sulfhydryls (NPSH) and predicted GSH levels following ip administration of naphthalene to a rat.

Treatment of mice with BSO depletes GSH in the liver more than in the lung. In naphthalene dosing experiments, GSH levels in lung and liver were 86 and 35 percent of the control values before administration of a 200 mg/kg dose of naphthalene (Buckpitt and Warren, et al., (1983) supra). The results of this experiment were compared to the simulation. Simulation predicts an increase in covalent binding from 202 to 510 pmole/mg (factor of 2.52) in the lung, and the experiments show an increase from 137 to 411 pmole/mg (factor of 3.0). In the liver, predicted binding levels are 156 and 1387 pmole/mg, and the observed levels are 255 and 1069 pmole/mg.

Simulation of pretreatment with xylene showed no significant changes in covalent binding or GSH depletion following 300 mg/kg naphthalene ip. Similar results have been observed experimentally (Buckpitt and Warren, et al., 1983, supra).

A comparison of covalent binding levels determined by experiment and simulation at or near the $LD_{50}$s appears in Table 8.

TABLE 8

Comparison of Covalent Binding in the Lung for $LD_{50}$s.

| | Binding in pmole/mg | |
|---|---|---|
| Male mouse, po, bioavailability 70% | 335, | 544 |
| Female mouse, po, bioavailability 81% | 668, | 842 |
| Male rat, po, bioavailability 70% | 277, | 304 |
| Male rat, po, bioavailability 81% | 296, | 321 |
| Male mouse, ip (simulated) | 453 | |
| Male Swiss-Webster mouse, ip, 300 mg/kg[a] | 675 | |
| Male Swiss-Webster mouse, ip, 400 mg/kg[b] | 912 | |
| Oral uptake rates of 0.01155 and 0.005775/min | | |

[a]Data of O'Brien et al., 1985, supra
[a]Data of Warren et al., 1982, supra

Sensitivity Analysis

Three test cases were chosen for sensitivity analysis of the mouse PBPK. These were the overall disposition of a 100 mg/kg ip dose of naphthalene and the results of administration of 200 and 400 mg/kg naphthalene ip, especially the covalent binding levels resulting from these two doses.

Decreasing the initial concentration of GSH in the lung from 2.2 mM to 1.3 mM, the lowest value reported in the literature (Richieri and Buckpitt, et al., 1988, supra) did not significantly change the results of the simulation.

Figure 27:
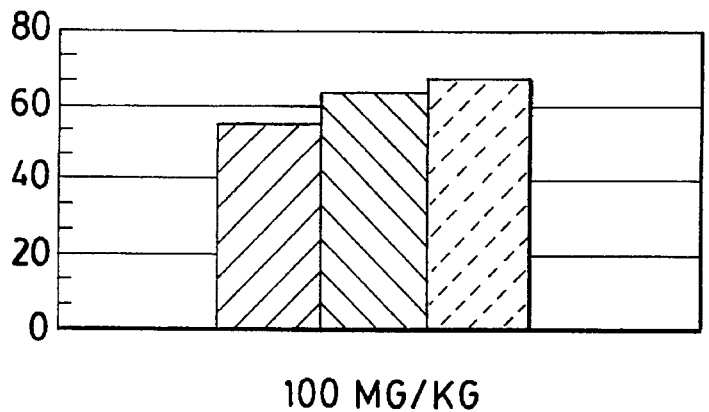
FIG. 27 is a bar graph of the sensitivity of naphthalene disposition at a 100 mg/kg ip injection level to initial GSH levels of 4.1 mM, 6.6 mM, and 8.6 mM in mouse liver.
Figure 28:
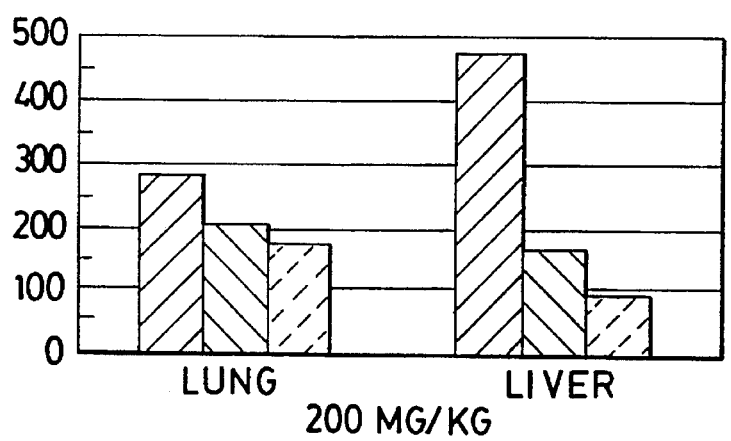
FIG. 28 is a bar graph of the sensitivity of covalent binding levels four hours after 200 mg/kg ip injection of naphthalene to initial GSH levels of 4.1 mM, 6.6 mM, and 8.6 mM in mouse lung and liver.
Figure 29:
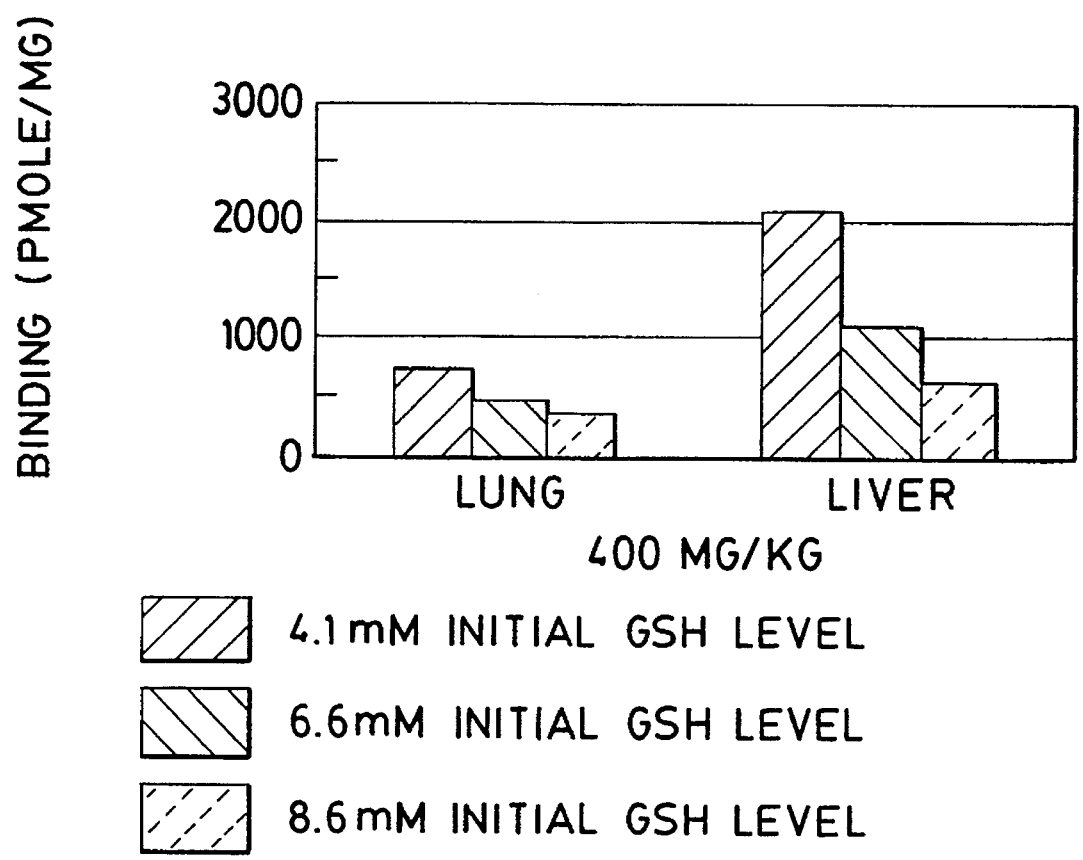
FIG. 29 is a bar graph of the sensitivity of covalent binding levels four hours after 400 mg/kg ip injection of napthalene to initial GSH levels of 4.1 mM, 6.6 mM, and 8.6 mM in mouse lung and liver.

The effects of changing the initial concentration of liver GSH are shown in FIGS. 27–29. The GSH levels used (4.1 and 8.6 mM) are the lowest and highest values found in the literature (Buonarati et al., 1989, supra, and Richieri and Buckpitt, et al., 1987, supra).

Doubling or halving the blood volume did not significantly affect the results.

The highest prediction of cardiac output for a mouse, 27.7 ml/min, results from scaling the cardiac output used by Andersen et al., 1987, supra. Percentages of cardiac output flowing to each tissue group were kept constant. For the 100 mg/kg dose, the concentration in the fat two hours after administration increases from 5.1 mM to 8.1 mM when the cardiac output is increased. Decreases in binding are observed at the 200 and 400 mg/kg doses. At the lower dose, the lung and liver binding levels drop to 39 and 66 percent of the values determined in the base model. For the higher dose, binding levels decrease to 43 and 41 percent of the lung and liver binding in the base model.

Increasing the blood flow to the fat and decreasing blood flow to the "Other Tissues" while keeping cardiac output constant also increases concentrations in the fat and decreases covalent binding.

A change in lung weight does not significantly affect covalent binding, but a shift in the RS/SR ratio for the overall disposition of a 100 mmg/kg dose of naphthalene does occur. If the lung weight is decreased to 0.125 g, the ratio of conjugate 2 to conjugates 1 and 3 is 1.03, but if it is increased to 0.5 g the ratio increases to 1.11.

Increasing the fat:blood partition coefficient from 796 to 7960 had virtually no effect. When decreased to 79.6, the naphthalene concentration in the fat decreased from 5.1 to 3.2 mM two hours after administration of a 100 mg/kg dose.

DISCUSSION

By slightly modifying the GSH resynthesis model of D'Souza et al., 1988, supra, we were able to match experimental observations quite well. A good fit was achieved in terms of levels of GSH and the known characteristics of GSH resynthesis—slight overshoot for hepatic GSH before declining to steady state levels, and a more gradual increase in lung GSH without the over shoot (D'Souza et al., 1988, supra). One of the modifications, decreasing the degradation rate of lung GSH has a physiological basis—the turnover time for GSH in the lung is longer than in the liver (Griffith and Meister, 1979, supra.), The parameters for naphthalene biotransformation in the mouse lung give a better fit to the RS/SR ratio than to reaction rates. A compromise between the two was necessary, and it was decided that the ratio was the more important characteristic. The high RS/SR ratio is what is distinctive about metabolism in the mouse lung, compared to other tissues and other species. Also, the simulation of xylene pretreatment demonstrates that the reaction rate in the lung does not have a major impact on the overall process.

Brief incubations with lung microsomes can be somewhat misleading, as can be seen in Table 5. The simulation shows that fairly high levels of naphthalene oxide are present at six minutes. In these incubations, the reaction is "stopped" at six minutes by addition of ice cold methanol (Buckpitt, et al., 1984, supra). While this should effectively stop the enzymatic reaction, non-enzymatic reaction to covalently bound adducts and 1-naphthol will continue, albeit at a much slower rate. If assays are not done promptly, the naphthalene oxide will rearrange, giving inappropriately high levels of 1-naphthol and covalently bound adducts.

We found that a relatively rapid oral uptake was needed to see much difference in GSH conjugation between the 75 and 200 mg/kg doses (Table 7). However, if the uptake was too rapid, the recovery of the liver GSH would be well on its way by 6½ hours after po administration. As a compromise, values of 1–2 hours for absorption half-time were used in other oral simulations.

The PBPK simulated whole animal toxicology quite well. The estimate for GSH conjugates of a 100 mg/kg dose was a bit high, but decreasing the initial value of liver GSH from 6.6 to 4.1 mM decreases the percent recovered as GSH conjugates from 64 to 57 percent. This is in the range predicted by combining the results of Stillwell, et al., 1982, supra and Buonarati et al., 1990, supra.

The simulations of covalent binding over a range of doses are also quite accurate. The sharp increases in covalent binding occur between 200 and 400 mg/kg for both the experiments and simulations (FIGS. 21 and 22) and the simulation predicts the binding levels in the liver quite well. The model underpredicts covalent binding and overpredicts GSH levels in the lung at higher doses (FIGS. 21 and 23). This suggests that the model assumption of equilibrium between blood and lung for naphthalene oxide concentrations may not be entirely accurate, or that the partition coefficient is too low.

The simulation of pretreatments also matches the available in vivo data. Similar increases in binding after depletion of GSH were observed in the lung for simulation and experiment. In terms of percent increase, the liver binding was way off, but the nature of the increase was the same (binding levels of less than 300 pmole/mg without BSO, over 1000 pmole/mg with BSO).

Detailed whole animal and in vitro data for the rat is not as readily available as for the mouse, but the model does make a fairly accurate prediction of GSH levels in the rat after ip dosing (FIGS. 28 and 26).

Table 8 summarizes binding levels measured and predicted for doses at or near the $LD_{50}S$. Since all the simulations have the same weaknesses, it is probably more reliable to compare the simulations to each other than each to the experimentally determined values. All the simulations for male rodents show similar levels of binding in the lung. This suggests that the differences in rodent sensitivity to naphthalene are due to the pharmacokinetics, not to differences between mouse and rat target cells (Clara cells).

To summarize, we have developed a PBPK which accurately models the toxicology of naphthalene, providing a way to study species and route differences. This was accomplished by incorporating the circulation of reactive metabolites with existing GSH synthesis model. This model can be a paradigm for other compounds which exhibit similar mechanisms of toxicity.

EXAMPLE 3

An in vitro system like that shown in FIG. 3 was constructed without process control features. This system included reservoir 50, reservoir discharge conduit 52, pump 54, chamber 56, conduit 58, pump 62, valve 64, flow meter 66, chamber 68, conduit 70, pump 74, conduit 76, flow meter 78, valve 80, exhaust gas line 82, oxygen-containing gas supply tank 84, conduit 86, and flow meter 88.

Reservoir 50 was provided with modified eagle's medium, supplemented with 10% fetal bovine serum and 10% calf serum. The contents of the reservoir were then aerated with a mixture of 5% carbon dioxide in air from tank 84. H4IIE cells, a rat hepatoma cell line, were grown to near confluence in chambers 56 and 68, respectively. Adequate mixing in chamber 68 was achieved with a Teflon stir bar and a magnetic stir plate, while blending in chamber 56 was achieved with a rotating platform. A temperature of 37° C. was maintained in reservoir 50 by circulating antifreeze at that temperature through the jacket of reservoir 50. Chambers 56 and 68 were wrapped with heating tape.

Pumps 54, 62, and 74 were operated to circulate 7 ml/min of culture medium from reservoir 50 to chamber 56, 9.5 ml/min of culture medium out of chamber 56, 7 ml/min of culture medium in conduit 76, 2.5 ml/min of culture medium into chamber 68, and 2.5 ml/min of culture medium in conduit 70. The flow of oxygen-containing gas in conduit 86 is at a rate of 15 ml/min.

After seven hours, the circulating culture medium was sampled at different points in the system, pumps 54, 62, and 74 were shut off, and chambers 56 and 68 were disconnected from the system. The cells in the chambers were immediately trypsinized and placed in plastic tissue culture dishes. Within 2½ hours, almost all the cells had reattached to the plastic tissue culture dishes. Media volumes were measured and tabulated as set forth in Table 9 below.

TABLE 9

| | Initial Media Volume | Media pH at 0 Hours | Media pH at 7 Hours |
|---|---|---|---|
| Reservoir 50 | 35 | 7.74 | 7.55 |
| Chamber 56 | 20 | 7.74 | 7.47 |
| Chamber 68 | 235 | 7.51 | 7.60 |

This experiment demonstrates that pH can be adequately controlled by aerating media reservoir 50 with air containing 5% carbon dioxide. The ability of the cells to reattach shows that conditions necessary to keep cells healthy and functional are being achieved in this system.

EXAMPLE 4

The equipment of Example 3 was modified to eliminate valve 64, flow meter 66, chamber 68, conduit 70, and pump 74. Instead, material discharged from pump 62, which does not enter conduit 76, travels through a conduit to a hollow fiber unit (e.g., Amicon vitafiber model 3S100 hollow fiber unit) which contains H4IIE cells. Such material then passes through a flow meter, and back to chamber 56 which contains LL/2 cells, a mouse lung epithelial cell line, which has been grown near confluence with Dulbecco's Modified Eagle's medium with 10% calf serum. The H4IIE cells, a rat hepatoma cell line, were inoculated into the Amicon hollow fiber unit, allowed to attach, and cultured using Modified Eagle's Medium supplemented with 10% fetal bovine serum and 10% calf serum for 24 hours before use. Reservoir 50 was filled with 50% Modified Eagle's Medium and 50% Dulbecco's Modified Eagle's Medium supplemented with 5% fetal bovine serum and 10% calf serum. The culture medium within reservoir 50 was aerated with a mixture of 5% carbon dioxide in air. The contents of reservoir 50 were mixed with a Teflon stir bar and a magnetic stir plate and circulated. The temperature of reservoir 50 and chamber 56 were maintained in substantially the same fashion as discussed with respect to Example 3.

Pumps 54 and 62 were operated to circulate 8.5 ml/min of culture medium from reservoir 50 to chamber 56, 11 ml/min of culture medium out of chamber 56, 8.5 ml/min of culture medium in conduit 76, 2.5 ml/min of culture medium into the hollow fiber unit, and 2.5 ml/min of culture medium from the hollow fiber unit to chamber 56. The flow of oxygen-containing gas in conduit 86 is at a rate of 15 ml/min.

After seven hours, pumps 54 and 62 were turned off and the cell-containing compartments disconnected from the system. The H4IIE cells were immediately trypsinized and placed in plastic tissue culture dishes. Within two hours, most of the cells reattached to the plastic tissue culture dishes. The LL/2 cells were viewed under a microscope and the attached cells had a morphology comparable to control cells maintained in an incubator.

The use of a hollow fiber unit substantially reduces the culture medium volume necessary to operate the system. This experiment also demonstrates the modularity of the present invention by showing that different components can be used while maintaining the basic layout of the system. The ability of the cells to reattach shows the conditions necessary to keep them healthy and functional, are maintained in the hollow fiber unit.

Although the invention has been described in detail for the purpose of illustration, it is understood that such detail is solely for that purpose, and variations can be made therein by those skilled in the art without departing from the spirit and scope of the invention which is defined by the following claims.

What is claimed is:

1. An in vitro system which maintains different cell types in a viable state comprising:

a plurality of cell culture chambers each containing the different cell types in a culture medium containing a substance to be evaluated;

a gas-liquid exchange device;

a conduit system to conduct culture medium between said gas-liquid exchange device and said plurality of cell culture chambers;

a circulation mechanism for circulating culture medium through said conduit system, said plurality of cell culture chambers, and said gas-liquid exchange device, including circulating culture medium between said plurality of cell culture chambers, wherein the substance to be evaluated contacts the different cell types, thereby producing either metabolites of the substance to be evaluated or metabolites of the different cell types; and a microprocessor to control operation of said gas-liquid exchange device and said circulation mechanism, wherein said plurality of cell culture chambers, said conduit system, and said circulation mechanism are configured such that the metabolites of the different cell types or the metabolites of the substance to be evaluated are exchanged between said plurality of cell culture chambers.

2. An in vitro system according to claim 1, wherein one of said plurality of cell culture chambers contains lung cells.

3. An in vitro system according to claim 2, wherein said conduit system connects the cell culture chamber containing lung cells with the gas-liquid exchange device and with one or more of said plurality of cell culture chambers each containing different types of cells.

4. An in vitro system according to claim 3, wherein one of said plurality of cell culture chambers contains liver cells.

5. An in vitro system according to claim 3, wherein the one or more of said plurality of cell culture chambers each containing different types of cells are arranged in parallel with respect to one another.

6. An in vitro system according to claim 2, wherein the lung cells are pulmonary Clara cells, pulmonary macrophages, or Type II cells.

7. An in vitro system according to claim 1, wherein one of said plurality of cell culture chambers contains liver cells.

8. An in vitro system according to claim 1, wherein one of said plurality of cell culture chambers contains cells transfected with a human gene.

9. An in vitro system according to claim 1, wherein said circulation mechanism includes one or more pumps to withdraw culture medium from said plurality of cell culture chambers.

10. An in vitro system according to claim 9, wherein said circulation mechanism further includes means to pressurize said gas-liquid exchange device to a level sufficient for culture medium to flow through said conduit system to said plurality of cell culture chambers without aid of a pump.

11. A method for physiological and metabolic evaluation of a substance comprising:

providing an in vitro system for physiological and metabolic evaluation of substances, said system comprising:

a plurality of cell culture chambers each containing different types of cells in a culture medium;

a gas-liquid exchange device;

a conduit system to conduct culture medium between said gas-liquid exchange device and said plurality of cell culture chambers;

a circulation mechanism for circulating culture medium through said conduit system; and a microprocessor to control operation of said gas-liquid exchange device and said circulation mechanism;

adding a substance to be evaluated to the culture medium of said in vitro system;

circulating the culture medium containing the substance through said plurality of cell culture chambers, said gas-liquid exchange device, and said conduit system with said circulation mechanism, wherein the substance to be evaluated contacts the different types of cells, thereby producing either metabolites of the substance to be evaluated or metabolites of the different types of cells and the metabolites of the different types of cells or the metabolites of the substance to be evaluated are exchanged between said plurality of cell culture chambers; and evaluating the cells in each of said plurality of cell culture chambers or the culture medium for physiological and metabolic changes resulting from the presence of the substance in the culture medium.

12. A method according to claim 11, wherein said evaluating comprises determining the efficacy of the substance which is a biologically active compound.

13. A method according to claim 11, wherein said evaluating comprises determining the toxicity of the substance which is a biologically active compound.

14. A method according to claim 11, wherein said evaluating comprises determining the sensitivity of cells in said plurality of cell culture chambers to the substance which is a biologically active compound.

15. A method according to claim 11, wherein said evaluating comprises determining the efficacy of a multiple dose regimen of the substance.

16. A method according to claim 11, wherein one of said plurality of cell culture chambers contains lung cells.

17. A method according to claim 16, wherein said conduit system connects the cell culture chamber containing lung cells with the gas-liquid exchange device and with one or more of said plurality of cell culture chambers each containing different types of cells.

18. A method according to claim 17, wherein one of said plurality of cell culture chambers contains liver cells.

19. A method according to claim 17, wherein the one or more of said plurality of cell culture chambers each containing different types of cells are arranged in parallel with respect to one another.

20. A method according to claim 16, wherein the lung cells are pulmonary Clara cells, pulmonary macrophages, or Type II cells.

21. A method according to claim 11, wherein one of said plurality of cell culture chambers contains cells transfected with a human gene.

22. An in vitro system which maintains different cell types in a viable state comprising:

a plurality of cell culture chambers each suitable for containing the different cell types in a culture medium containing a substance to be evaluated;

a gas-liquid exchange device;

a conduit system suitable for conducting culture medium between said gas-liquid exchange device and said plurality of cell culture chambers;

a circulation mechanism for circulating culture medium through said conduit system, said plurality of cell culture chambers, and said gas-liquid exchange device, including circulating culture medium between said plurality of cell culture chambers, wherein the circulation mechanism is capable of selectively providing a flow of culture medium directly between at least two of said plurality of culture chambers or from one culture chamber through the gas-liquid exchange device and through another culture chamber and wherein the substance to be evaluated contacts the different cell types, thereby producing either metabolites of the substance to be evaluated or metabolites of the different cell types; and a microprocessor to control operation of said gas-liquid exchange device and said circulation mechanism, wherein said plurality of cell culture chambers, said conduit system, and said circulation mechanism are configured such that the metabolites of the different cell types or the metabolites of the substance to be evaluated are exchanged between said plurality of cell culture chambers.

23. An in vitro system according to claim 22 further comprising:

a cabinet surrounding elements of said system to maintain sterile conditions in said system.

24. An in vitro system comprising:

a plurality of cell culture chambers each containing different cells in a culture medium containing a substance to be evaluated;

a reservoir for contacting the culture medium with a gas and from which by-product gases are removed;

a conduit system to conduct culture medium between said reservoir and said plurality of cell culture chambers;

a circulation mechanism for circulating culture medium through said conduit system, said plurality of cell culture chambers, and said reservoir, including circulating culture medium between said plurality of cell culture chambers, wherein the substance to be evaluated contacts the different cells, thereby producing either metabolites of the substance to be evaluated or metabolites of the different cells; and a microprocessor to control operation of said reservoir and said circulation mechanism, wherein said plurality of cell culture chambers, said conduit system, and said circulation mechanism are configured such that the metabolites of the different cells or the metabolites of the substance to be evaluated are exchanged between said plurality of cell culture chambers.

25. A method for physiological and metabolic evaluation of a substance comprising:

providing an in vitro system for physiological and metabolic evaluation of substances, said system comprising:

a plurality of cell culture chambers each containing cells in a culture medium;

a reservoir for contacting the culture medium with a gas and from which by-product gases are removed;

a conduit system to conduct culture medium between said reservoir and said plurality of cell culture chambers;

a circulation mechanism for circulating culture medium through said conduit system; and a microprocessor to control operation of said reservoir and said circulation mechanism;

adding a substance to be evaluated to the culture medium of said in vitro system;

circulating the culture medium containing the substance through said plurality of cell culture chambers, said reservoir, and said conduit system with said circulation mechanism, wherein the substance to be evaluated contacts the cells, thereby producing either metabolites of the substance to be evaluated or metabolites of the cells and the metabolites of the cells or the metabolites of the substance to be evaluated are exchanged between said plurality of cell culture chambers; and evaluating the cells in each of said plurality of cell culture chambers or the culture medium for physiological and metabolic changes resulting from the presence of the substance in the culture medium.

26. An in vitro system comprising:

a plurality of cell culture chambers each suitable for containing different cell types in a culture medium containing a substance to be evaluated;

a reservoir suitable for contacting the culture medium with a gas and from which by-product gases are removed;

a conduit system suitable for conducting culture medium between said reservoir and said plurality of cell culture chambers;

a circulation mechanism for circulating culture medium through said conduit system, said plurality of cell culture chambers, and said reservoir, including circulating culture medium between said plurality of cell culture chambers, wherein the circulation mechanism is capable of selectively providing a flow of culture medium directly between at least two of said plurality of culture chambers or from one culture chamber through the gas-liquid exchange device and through another culture chamber and wherein the substance to be evaluated contacts the different cell types, thereby producing either metabolites of the substance to be evaluated or metabolites of the different cell types; and a microprocessor to control operation of said reservoir and said circulation mechanism, wherein said plurality of cell culture chambers, said conduit system, and said circulation mechanism are configured such that the metabolites of the different cell types or the metabolites of the substance to be evaluated are exchanged between said plurality of cell culture chambers.

* * * * *